US010932946B2

United States Patent
M Sina Raja et al.

(10) Patent No.: US 10,932,946 B2
(45) Date of Patent: Mar. 2, 2021

(54) DEVICE FOR INSERTION INTO A BODY CAVITY, AND METHOD OF FABRICATION THEREOF

(71) Applicants: Agency for Science, Technology and Research, Singapore (SG); National University Hospital (Singapore) Pte Ltd, Singapore (SG); Singapore Health Services Pte Ltd, Singapore (SG)

(72) Inventors: Prusothman M Sina Raja, Singapore (SG); Angela Renayanti Dharmawan, Singapore (SG); Chee Keong Tee, Singapore (SG); Yao Wang, Singapore (SG); Sheau Huei Frances Lim, Singapore (SG); Zhengtao Keith Chong, Singapore (SG)

(73) Assignees: Agency for Science, Technology and Research, Singapore (SG); National University Hospital (Singapore) Pte Ltd, Singapore (SG); Singapore Health Services Pte Ltd, Singapore (SG)

( * ) Notice: Subject to any disclaimer, the term of this patent is extended or adjusted under 35 U.S.C. 154(b) by 239 days.

(21) Appl. No.: 15/748,513

(22) PCT Filed: Jul. 29, 2016

(86) PCT No.: PCT/SG2016/050371
§ 371 (c)(1),
(2) Date: Jan. 29, 2018

(87) PCT Pub. No.: WO2017/023206
PCT Pub. Date: Feb. 9, 2017

(65) Prior Publication Data
US 2019/0000668 A1    Jan. 3, 2019

(30) Foreign Application Priority Data

Jul. 31, 2015   (SG) .............................. 10201506008

(51) Int. Cl.
*A61F 7/12*   (2006.01)
*A61F 7/10*   (2006.01)
(Continued)

(52) U.S. Cl.
CPC .............. *A61F 7/123* (2013.01); *A61F 7/106* (2013.01); *A61F 7/12* (2013.01); *A61M 31/00* (2013.01);
(Continued)

(58) Field of Classification Search
CPC ........ A61F 2007/005; A61F 2007/0028; A61F 2007/0048
See application file for complete search history.

(56) References Cited

U.S. PATENT DOCUMENTS 47,540 A * 5/1865 Gilbert .................... A61M 5/44
604/113
969,134 A * 8/1910 Cowie ...................... A61F 7/12
604/113
(Continued)

FOREIGN PATENT DOCUMENTS

CN     101657164 A    2/2010
CN     202397589 U    8/2012
(Continued)

OTHER PUBLICATIONS

International Preliminary Report on Patentability for International Application No. PCT/SG2016/050371 dated Feb. 6, 2018, pp. 1-6.
(Continued)

*Primary Examiner* — Kaitlyn E Smith
(74) *Attorney, Agent, or Firm* — Winstead PC

(57) ABSTRACT

There is provided a device for insertion into a body cavity, the device includes an insertion member configured to be inserted into the body cavity, an expandable member coupled to the insertion member, the expandable member
(Continued)

capable of being expanded to apply pressure onto tissue within the body cavity, a first member configured for storing a first endothermic reactant therein, and a second member configured for storing a second endothermic reactant therein. In particular, the first and second members are configured to, in a state of the device (e.g., compressed state), allow the first and second endothermic reactants to cooperate to effect an endothermic reaction to generate an endothermic product. Furthermore, the expandable member is configured to receive at least one of the first or second endothermic reactant and the endothermic product through a channel within the insertion member. There is also provided a method of fabricating a device for inserting into a body cavity.

18 Claims, 22 Drawing Sheets

(51) Int. Cl.
*A61M 31/00* (2006.01)
*A61F 7/00* (2006.01)
*A61F 7/02* (2006.01)

(52) U.S. Cl.
CPC .......... *A61F 2007/0091* (2013.01); *A61F 2007/0092* (2013.01); *A61F 2007/0258* (2013.01); *A61F 2007/0261* (2013.01); *A61F 2007/0276* (2013.01); *A61F 2007/101* (2013.01)

(56) References Cited

U.S. PATENT DOCUMENTS

| | | | | |
|---|---|---|---|---|
| 1,593,368 | A * | 7/1926 | Steinmetz et al. | A61F 7/123 607/104 |
| 1,729,296 | A * | 9/1929 | Sarason | A61F 7/123 607/105 |
| 3,348,542 | A * | 10/1967 | Jackson | A61M 16/0438 128/207.15 |
| 3,799,170 | A * | 3/1974 | Walsh | A61M 29/02 606/193 |
| 3,939,842 | A * | 2/1976 | Harris | A61F 5/0093 607/113 |
| 4,060,080 | A * | 11/1977 | Akiyama | A61F 11/10 128/865 |
| 4,563,182 | A * | 1/1986 | Stoy | A61F 5/0093 424/436 |
| 4,692,336 | A * | 9/1987 | Eckenhoff | A61K 9/0004 424/468 |
| 4,696,302 | A | 9/1987 | Clark et al. | |
| 4,841,970 | A | 6/1989 | Rand | |
| 4,938,221 | A * | 7/1990 | Tuffel | A61F 7/123 606/197 |
| 5,062,425 | A * | 11/1991 | Tucker | A61F 7/123 604/103.11 |
| 5,192,266 | A | 3/1993 | Wilk | |
| 5,335,669 | A * | 8/1994 | Tihon | A61B 5/01 600/549 |
| 6,009,351 | A * | 12/1999 | Flachman | A61B 18/1815 607/101 |
| 8,728,140 | B2 * | 5/2014 | Feemster | A61F 6/08 607/113 |
| 9,066,843 | B1 * | 6/2015 | Greco | A61H 19/44 |
| 9,592,150 | B2 * | 3/2017 | McNulty, Jr. | A61F 7/12 |
| 9,888,927 | B2 * | 2/2018 | Belfort | A61B 17/12099 |
| 2004/0039430 | A1 | 2/2004 | Gonzales | |
| 2005/0021113 | A1 * | 1/2005 | Gonzales | A61F 7/123 607/105 |
| 2005/0177214 | A1 | 8/2005 | Pohler | |
| 2006/0212065 | A1 * | 9/2006 | Jao | A61F 7/103 606/197 |
| 2007/0021809 | A1 * | 1/2007 | Cole | A61F 7/12 607/113 |
| 2007/0203429 | A1 * | 8/2007 | Ziv | A61F 2/005 600/573 |
| 2012/0059394 | A1 | 3/2012 | Brenner et al. | |
| 2012/0209257 | A1 * | 8/2012 | van Der Weide | A61B 18/1815 606/23 |
| 2013/0023970 | A1 * | 1/2013 | Cull | A61F 7/10 607/113 |
| 2013/0338431 | A1 * | 12/2013 | Shalon | A61F 2/0009 600/32 |
| 2015/0209176 | A1 * | 7/2015 | McNulty, Jr. | A61F 7/12 607/113 |
| 2016/0067027 | A1 * | 3/2016 | Shalon | A61F 2/0009 600/32 |
| 2016/0193469 | A1 * | 7/2016 | Cardinal | A61N 5/02 607/46 |
| 2019/0247632 | A1 * | 8/2019 | Llaneza | A61M 31/00 |
| 2019/0261965 | A1 * | 8/2019 | Kabadayi | A61B 17/0057 |

FOREIGN PATENT DOCUMENTS

| | | |
|---|---|---|
| CN | 203107094 U | 8/2013 |
| DE | 3720346 A1 | 12/1988 |
| JP | 05096000 A | 4/1993 |
| JP | 2011206208 A | 10/2011 |
| UA | 72302 C2 | 2/2005 |
| WO | 9304727 A1 | 3/1993 |
| WO | 2004017876 A2 | 3/2004 |
| WO | 2006036063 A2 | 4/2006 |
| WO | 2008100433 A2 | 8/2008 |
| WO | 2013087031 A1 | 6/2013 |
| WO | 2013087032 A1 | 6/2013 |

OTHER PUBLICATIONS

Written Opinion for International Application No. PCT/SG2016/050371 dated Oct. 4, 2016, pp. 1-5.
Office Action for Chinese Patent Application No. 201680057625.9 dated Apr. 10, 2020, pp. 1-23.
Office Action for Japanese Patent Application No. 2018-504903 dated Jul. 1, 2020, pp. 1-9.

* cited by examiner

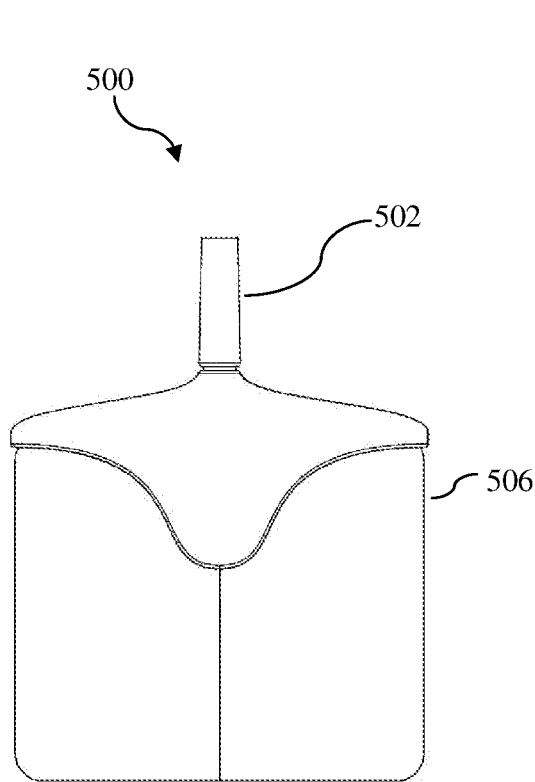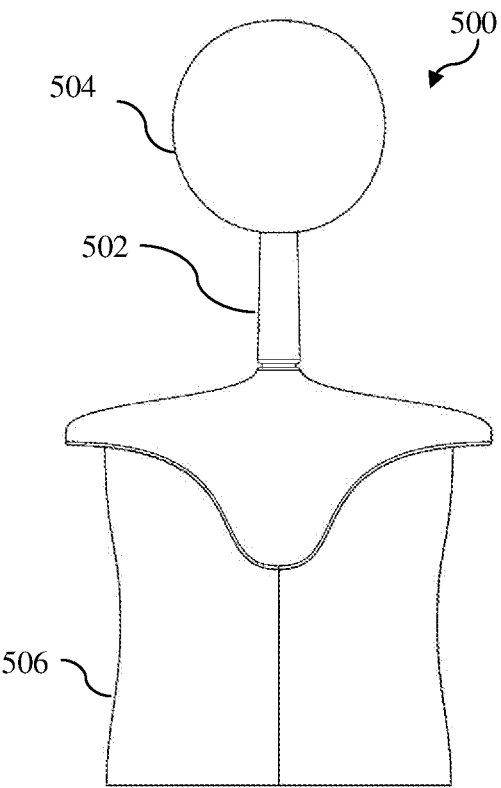
FIG. 5A
FIG. 5B
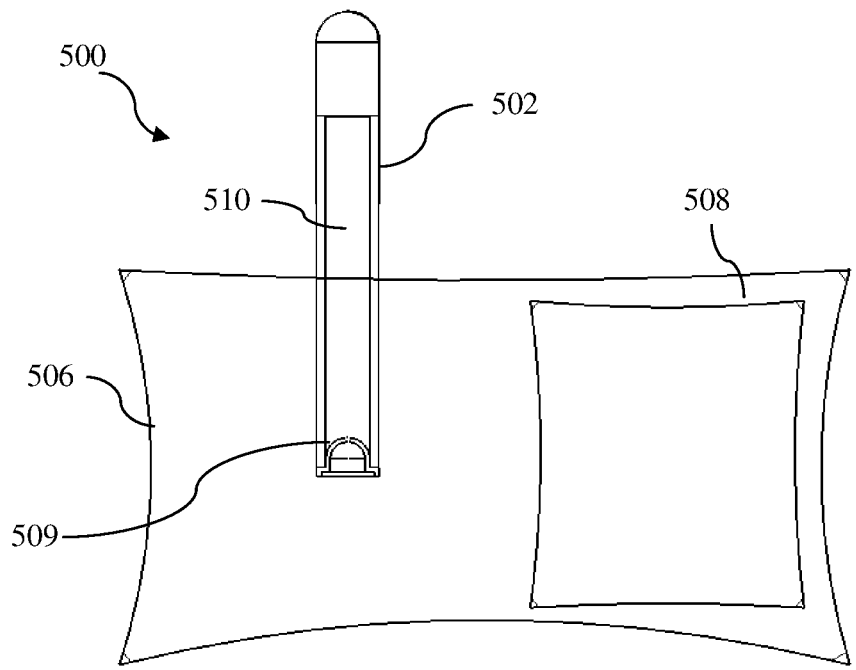
FIG. 5C

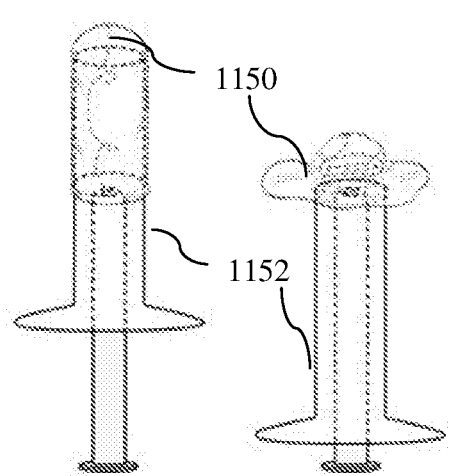 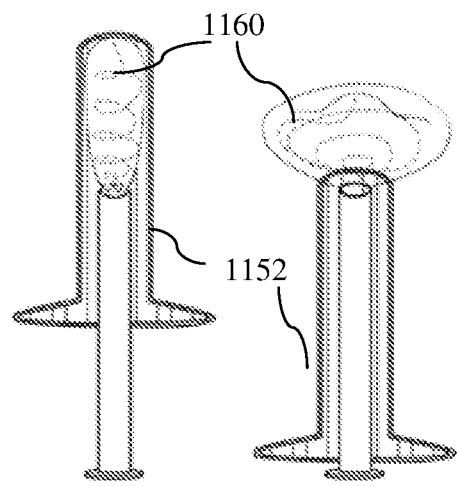
FIG. 11A FIG. 11B
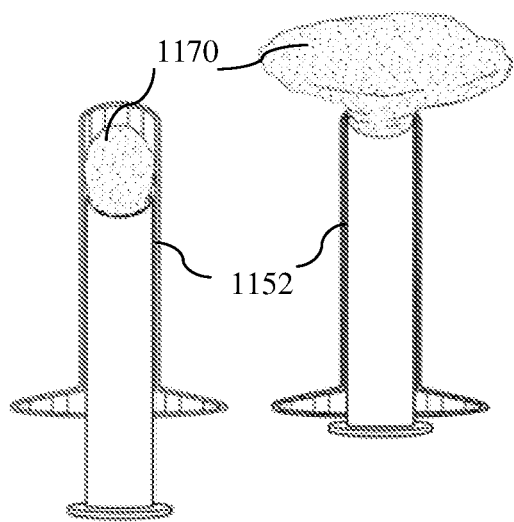
FIG. 11C

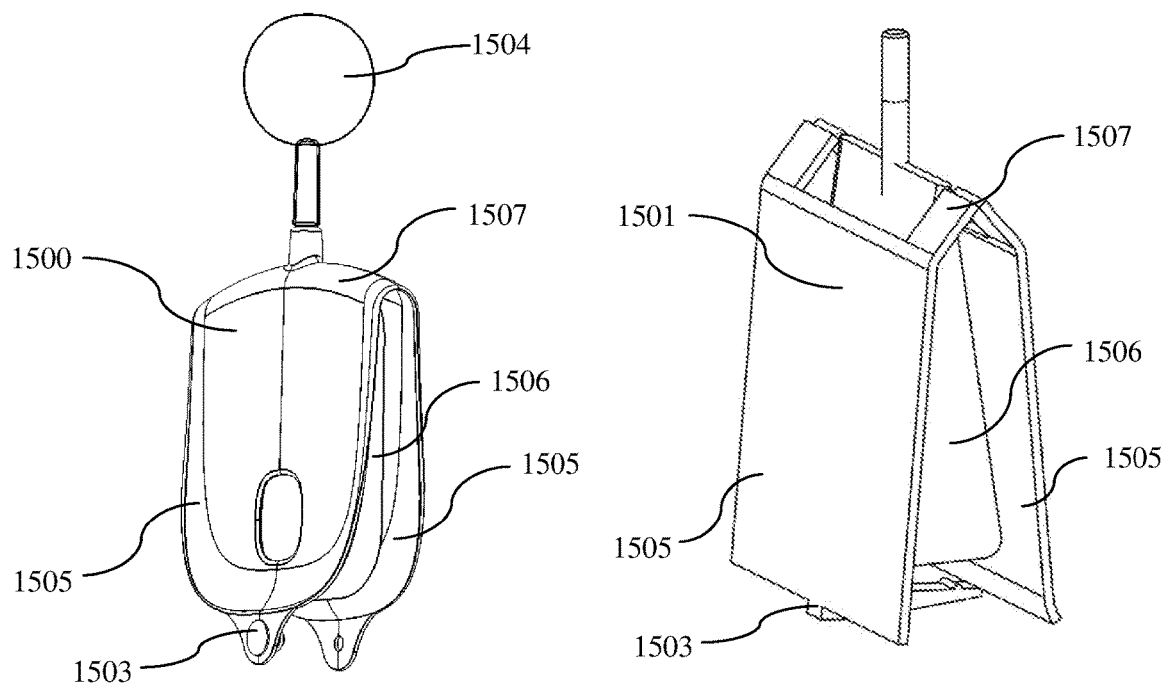
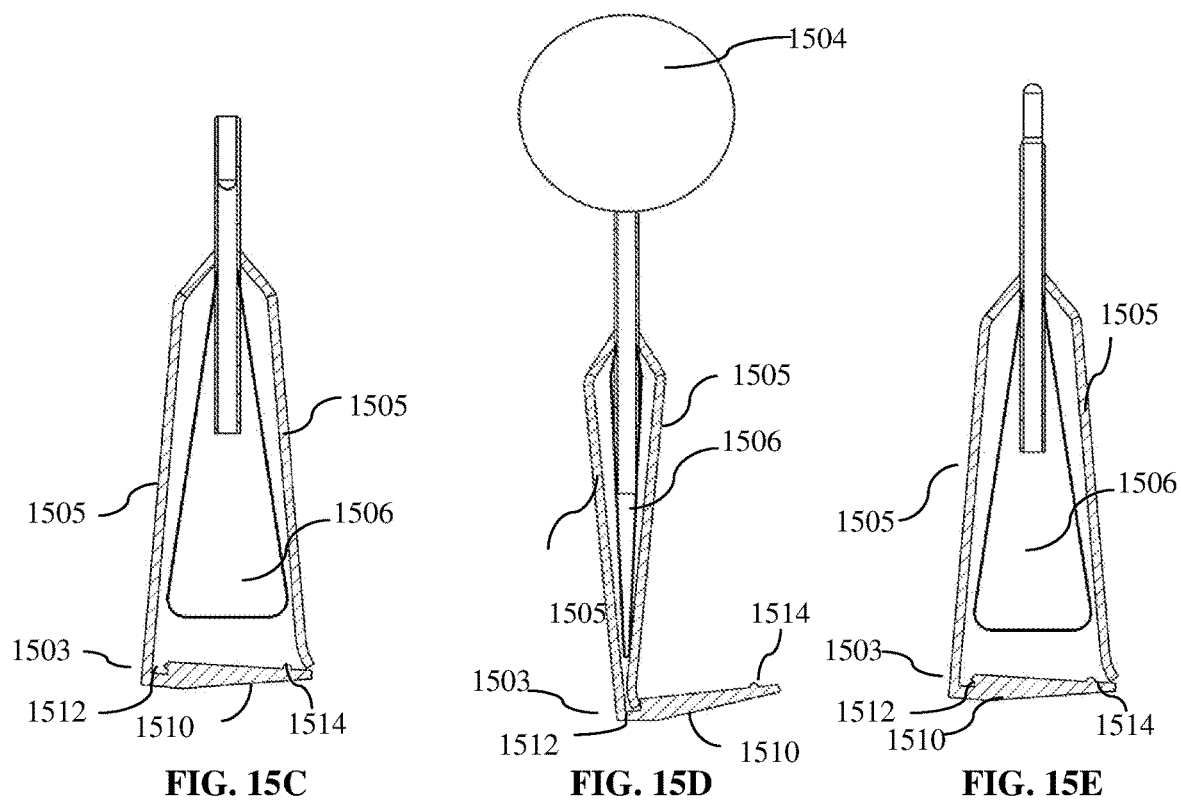
FIG. 15A   FIG. 15B   FIG. 15C   FIG. 15D   FIG. 15E

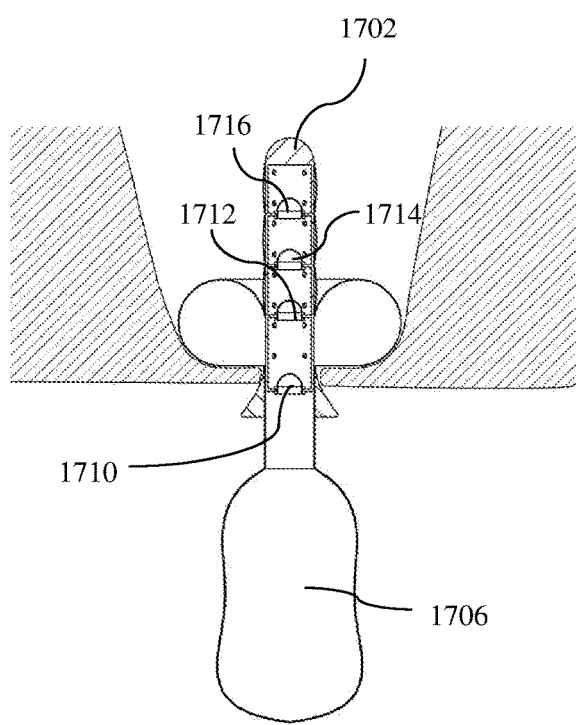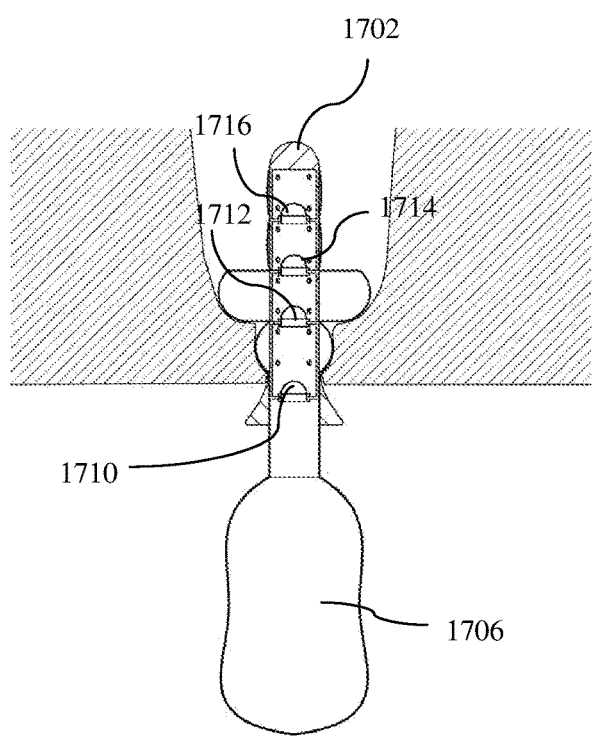
FIG. 17B                    FIG. 17C

DEVICE FOR INSERTION INTO A BODY CAVITY, AND METHOD OF FABRICATION THEREOF

CROSS-REFERENCE TO RELATED APPLICATION

This application claims the benefit of priority of Singapore Patent Application No. 10201506008X, filed 31 Jul. 2015, the content of which being hereby incorporated by reference in its entirety for all purposes.

TECHNICAL FIELD

The present invention generally relates to a device for insertion into a body cavity, such as into an anal canal for the treatment of hemorrhoids, and a method of fabricating the device.

BACKGROUND

Hemorrhoids are a plexus of dilated arteriovenous channels and connective tissue with the veins arising from the superior and inferior hemorrhoidal veins. They are located in the submucosal layer in the lower rectum and may be external or internal based upon whether they are below or above the dentate line. Internal hemorrhoids arise from the superior hemorrhoidal cushion. FIG. 1 depicts a schematic drawing illustrating an internal hemorrhoid 1 located at a distance inside the anal canal. Their three primary locations (left lateral, right anterior, and right posterior) correspond to the end branches of the middle and superior hemorrhoidal veins. The overlying mucosa is rectal, and innervation is visceral. Patients with hemorrhoids most commonly present with bright red bleeding per rectum, a prolapsing anal mass or pain.

Conventionally, early stage hemorrhoids may be treated with ointments or suppositories. However, ointments and suppositories are difficult to use or apply conventionally as the substance needs to be inserted using fingers in a difficult to access part of the body. As a result, the treatment or therapy may not be delivered efficiently or with ease and comfort.

A need therefore exists to provide a device for insertion into a body cavity that seeks to overcome, or at least ameliorate, one or more of the deficiencies of conventional devices or techniques. It is against this background that the present invention has been developed.

SUMMARY

According to a first aspect of the present invention, there is provided a device for insertion into a body cavity, the device comprising:

an insertion member configured to be inserted into the body cavity;

an expandable member coupled to the insertion member, the expandable member capable of being expanded to apply pressure onto tissue within the body cavity;

a first member configured for storing a first endothermic reactant therein; and a second member configured for storing a second endothermic reactant therein, wherein the first and second members are configured to, in a state of the device, allow the first and second endothermic reactants to cooperate to effect an endothermic reaction to generate an endothermic product, and wherein the expandable member is configured to receive at least one of the first or second endothermic reactant and the endothermic product through a channel within the insertion member.

In various embodiments, the first member has stored therein the first endothermic reactant, and the second member has stored therein the second endothermic reactant, separately from the first endothermic reactant.

In various embodiments, the device further comprises a separating member configured to, in a first state, block the first and second endothermic reactants from cooperating and, in a second state, allow the first and second endothermic reactants to cooperate to effect the endothermic reaction.

In various embodiments, the separating member is configured to be breakable to change from the first state to the second state.

In various embodiments, an opening of the second member is sealed by the separating member or the second member constitutes the separating member.

In various embodiments, at least the first member is configured to be compressible to cause the device to be in said state, wherein compressing the first member reduces a volume within the first member, thereby forcing the first endothermic reactant stored in the first member and/or the second endothermic reactant stored in the second member to flow to cooperate with each other to effect the endothermic reaction.

In various embodiments, the second member is located within the first member and is configured to be compressible to cause the device to be in said state, wherein compressing the first member at a region where the second member is located also compresses the second member, thereby reduces a volume within the second member and causes the separating member to break to allow the second endothermic reactant stored in the second member to flow out of the second member and into the first member to cooperate with the first endothermic reactant to effect the endothermic reaction.

In various embodiments, the second member is located within the first member and is configured to be non-compressible, wherein compressing the first member reduces the volume within the first member, thereby forcing the first endothermic reactant stored in the first member to flow into the second member, via an opening in the second member, to cooperate with the second endothermic reactant stored in the second member to effect the endothermic reaction.

In various embodiments, the device further comprises a structure for housing the first member.

In various embodiments, the structure comprises a latch mechanism configured to be releasably lockable between a lock state and a release state, and wherein in the lock state, the structure is configured to apply compressing pressure to compress the first member and maintain the first member in a compressed state, and in the release state, the structure is configured to house the first member without applying compressing pressure thereto.

In various embodiments, at least a portion of the expandable member comprises pores configured for allowing a therapeutic substance in the expandable member to discharge through the pores for delivery of the therapeutic substance to the tissue within the body cavity.

In various embodiments, the expandable member comprises an inner expandable layer and an outer expandable layer, wherein the inner expandable layer is arranged within the outer expandable layer, and the inner expandable layer and the outer expandable layer are configured to provide an outer compartment for storing a therapeutic substance therebetween for delivery of the therapeutic substance to the tissue within the body cavity.

In various embodiments, the outer expandable layer comprises pores configured for allowing the therapeutic substance between the inner expandable layer and the outer expandable layer to discharge through the pores for delivery of the therapeutic substance to the tissue within the body cavity.

In various embodiments, at least a portion of the outer expandable layer is made of a biodegradable material for allowing the therapeutic substance between the inner expendable layer and the outer expandable layer to escape for delivery of the therapeutic substance to the tissue within the body cavity when the biodegradable material is degraded.

In various embodiments, the expandable member is configured such that, prior to being expanded, an outer surface of the expandable member defines a receptacle, the receptacle configured for storing a therapeutic substance therein for delivery to the tissue within the body cavity when the expandable member is expanded.

In various embodiments, the device further comprises a valve configured to, in a first state, provide one-directional fluid flow through the valve from the first member.

In various embodiments, the device further comprises an external expandable member coupled to the insertion member at a predetermined distance from the distal end region, the external expandable member capable of being expanded to apply pressure onto an external region of the body cavity.

In various embodiments, the insertion member is configured so as to be adjustable in length.

In various embodiments, the insertion member comprises a plurality of compartments arranged successively along the insertion member, each compartment having coupled therewith a respective expandable member, each expandable member capable of being expanded in response to the at least one of the first or second endothermic reactant and the endothermic product received from the respective compartment, wherein a plurality of valve is arranged in the channel of the insertion member, each valve arranged between adjacent compartments associated therewith and configured to allow the at least one of the first or second endothermic reactant and the endothermic product to flow through the valve from a first compartment of the adjacent compartments to a second compartment of the adjacent compartment when a pressure acting on the valve is equal to or exceeds a threshold pressure, the first compartment being closer to the first member than the second compartment.

According to a second aspect of the present invention, there is provided a method of fabricating a device for inserting into a body cavity. The method comprising:

forming an insertion member configured to be inserted into the body cavity;

providing an expandable member coupled to the insertion member, the expandable member capable of being expanded to apply pressure onto tissue within the body cavity;

forming a first member configured for storing a first endothermic reactant therein; and forming a second member configured for storing a second endothermic reactant therein, and configuring the first and second members for allowing, in a state of the device, the first and second endothermic reactants to cooperate to effect an endothermic reaction to generate an endothermic product, wherein said providing an expandable member comprises configuring the expandable member to receive at least one of the first or second endothermic reactant and the endothermic product through a channel within the insertion member.

BRIEF DESCRIPTION OF THE DRAWINGS

Embodiments of the present invention will be better understood and readily apparent to one of ordinary skill in the art from the following written description, by way of example only, and in conjunction with the drawings, in which:

FIGS. 5A and 5B depict a schematic front view of a device for insertion into a body cavity according to an example embodiment of the present invention;

FIG. 5C depicts a schematic cross-sectional view of the device shown in FIGS. 5A and 5B;

FIGS. 11A to 11C depict schematic drawings of a mechanical expansion mechanism for various forms of expandable member according to various embodiments of the present invention;

FIG. 15A depicts a schematic perspective view of the device having a structure for housing the first member according to an example embodiment of the present invention;

FIG. 15B depicts a schematic perspective view of the device having a structure for housing the first member according to an another example embodiment of the present invention;

FIGS. 15C to 15E depict a schematic side view of the device shown in FIG. 15B at various states;

FIGS. 17A to 17C depict schematic drawings of a device for insertion into a body cavity whereby the insertion member is configured to have multiple compartments according to various embodiments of the present invention;

DETAILED DESCRIPTION

Embodiments of the present invention provide a device for insertion into a body cavity or natural orifice, and in particular but not limited to, an anal canal for the treatment of hemorrhoids. For example, various other types of applications include, but not limited to, the treatment of esophageal bleeding, epistaxis and benign prostate hyperplasia. For the sake of clarity, the device will be described herein for insertion into an anal canal for the treatment of hemorrhoids unless stated otherwise. However, it will be appreciated to a person skilled in the art that the device is not limited to such a specific application and various other applications such as those as mentioned above are also within the scope of the present invention.

Various embodiments of the present invention treat hemorrhoids by applying a constant pressure to the hemorrhoids for a certain/predetermined period of time to, for example, stop or reduce bleeding of the hemorrhoids. Therefore, embodiments of the present invention provide a device for insertion into an anal canal to provide mechanical/physical compression of or pressure to hemorrhoidal vessels for the treatment of hemorrhoids and rectal tissues. Once applied for a requisite period of time, the device may then be removed out of the anal canal to complete the treatment.

Figure 1:
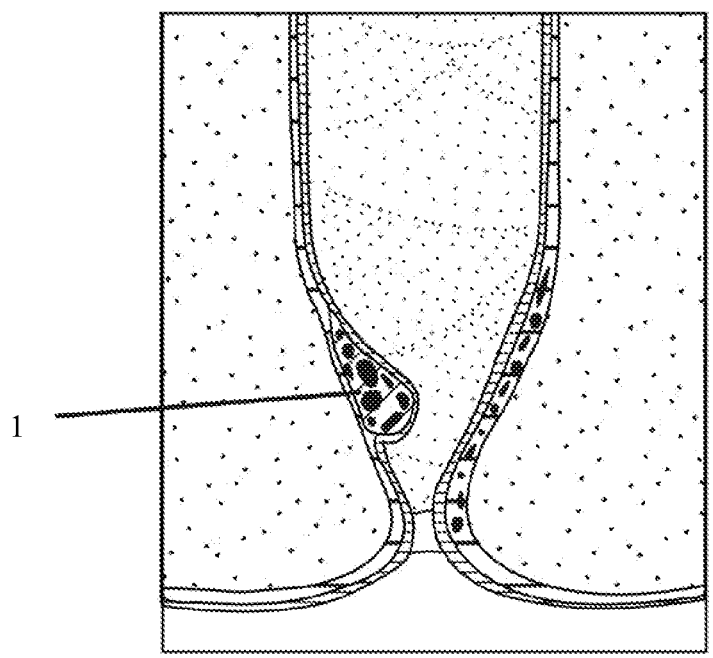
FIG. 1 depicts a schematic drawing illustrating an internal hemorrhoid located at a distance inside the anal canal as an example.
Figure 2:
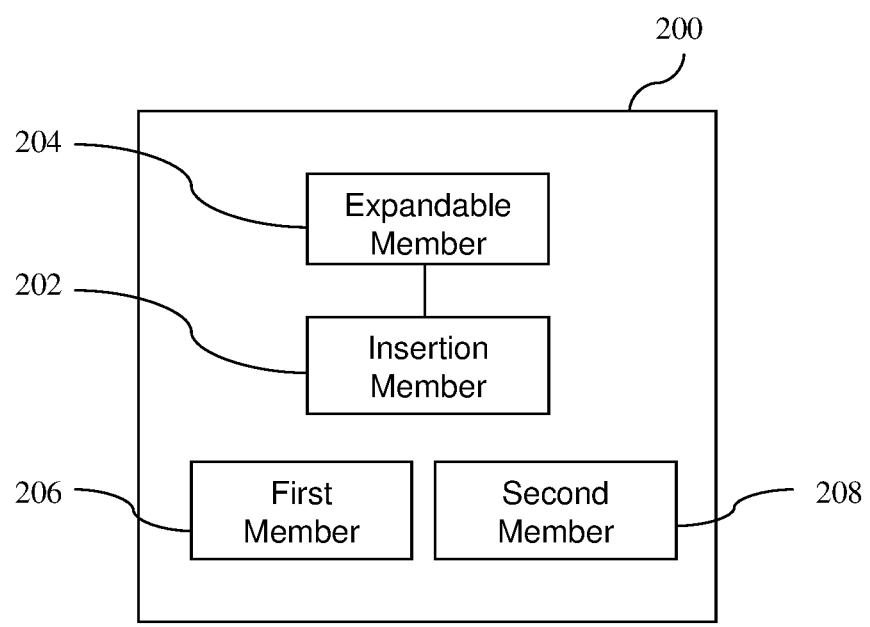
FIG. 2 depicts a schematic drawing of a device for insertion into a body cavity according to various embodiments of the present invention.

FIG. 2 depicts a schematic drawing of a device 200 for insertion into a body cavity according to various embodiments of the present invention. The device 200 comprises an insertion member 202 configured to be inserted into the body cavity, an expandable member 204 coupled to the insertion member 202 whereby the expandable member 204 is capable of being expanded to apply pressure onto tissue within the body cavity, a first member 206 configured for storing a first endothermic reactant therein, and a second member 208 configured for storing a second endothermic reactant therein. In particular, the first and second members 206, 208 in the device 200 are configured to, in a state of the device (e.g., in a compressed state) allow the first and second endothermic reactants to cooperate to effect an endothermic reaction to generate an endothermic product, and the expandable member 204 is configured to receive at least one of the first or second endothermic reactant (e.g., the fluid endothermic reactant) and the endothermic product through a channel within the insertion member 202.

Accordingly, the device 200 advantageously comprises an expandable member 204 which can be expanded/inflated to provide physical compression or pressure to the hemorrhoids for treating the hemorrhoids (e.g., to tamponade the bleeding) after the insertion member 202 has been inserted into the anal canal. Furthermore, as the expandable member 204 receives an endothermic product generated due to an endothermic reaction between the first and second endothermic reactants, a cold therapy is also applied to the hemorrhoids by the expandable member 204 to enhance the treatment. In various embodiments, since the first and second endothermic reactants are initially (e.g., before use or treatment) separately stored within the first and second members, respectively, and the first and second endothermic reactants are only caused to mix/cooperate to effect an endothermic reaction when performing the treatment (e.g., when preparing the device 200 to be inserted into the anal canal or after the insertion member 202 has been inserted into the anal canal at a desired location/position), an instant cold therapy can be applied to the hemorrhoids (in addition to the pressure) without requiring to refrigerate the device (or keep the device refrigerated). This is highly advantageous since the device can be conveniently stored at, for example, room temperature, thereby significantly improving the usability (e.g., convenience) and/or applicability of the device, such as in circumstances where a refrigerator is not available or conveniently accessible.

For the sake of clarity, the endothermic reaction will be described herein according to various embodiments of the present invention as being between a first endothermic reactant and a second endothermic reactant. However, it will be understood by a person skilled in the art that the endothermic reaction is not limited to involving only two endothermic reactants, and that additional reactant(s) may be involved for the endothermic reaction as appropriate or as desired and are within the scope of the present invention. It will also be appreciated to a person skilled in the art that a first endothermic reactant and a second endothermic reactant cooperating to effect an endothermic reaction is not limited to involving only the first and second endothermic reactants, and can include additional endothermic reactant(s) as long as the endothermic reaction involves at least the first and second endothermic reactants.

In various embodiments, at least the first member is configured to be compressible/deformable to cause the device to be in the compressed state, whereby compressing/deforming the first member reduces a volume within the first member thereby forcing the first endothermic reactant stored in the first member and/or the second endothermic reactant stored in the second member to flow to cooperate with each other to effect the endothermic reaction to generate the endothermic product. For example and without limitation, compressing/deforming the first member may be achieved by a user pressing or squeezing the first member, either directly or indirectly (such as via a structure supporting or housing the first member which will be described later according to various example embodiments of the present invention).

It will be appreciated that the first and second members 206, 208 may be configured/arranged in various configurations as long as the configuration/arrangement allows the first and second endothermic reactants to encounter to cooperate or mix so as to effect an endothermic reaction when the device is in the compressed state (e.g., by compressing/deforming the first member 206), and the expandable member 204 is able to receive the first or second endothermic reactant and/or the endothermic product, such as, for expanding the expandable member 204. It will also be appreciated that a configuration/arrangement allowing the first and second endothermic reactants to cooperate means that, for example, the first and second members 206, 208 are configured/arranged such that one or more fluid communication paths/openings exist or can be caused to exist (i.e., created) for the first and second endothermic reactants to encounter to cooperate. For example, it can be understood that such fluid communication paths/openings may be originally/initially (e.g., before the device is activated (before expandable member inflated)) blocked or sealed by, for example, adjustable/modifiable barriers, such as valve(s) and/or separating member(s)/membrane(s) (which will be described later), which are required to be adjusted (e.g., by an applied force or by deforming) or modified (e.g., by breaking) in order to unblock or create the fluid communication path(s)/opening(s).

In order that the present invention may be readily understood and put into practical effect, various embodiments of the present inventions will be described hereinafter by way of examples only and not limitations. It will be appreciated by a person skilled in the art that the present invention may, however, be embodied in various different forms/configurations and should not be construed as limited to the example embodiments set forth hereinafter. Rather, these example embodiments are provided so that the present disclosure will be thorough and complete, and will fully convey the scope of the present invention to those skilled in the art.

It will be appreciated to a person skilled in the art that the terminology used herein is for the purpose of describing various embodiments only and is not intended to be limiting of the present invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Figure 3A:
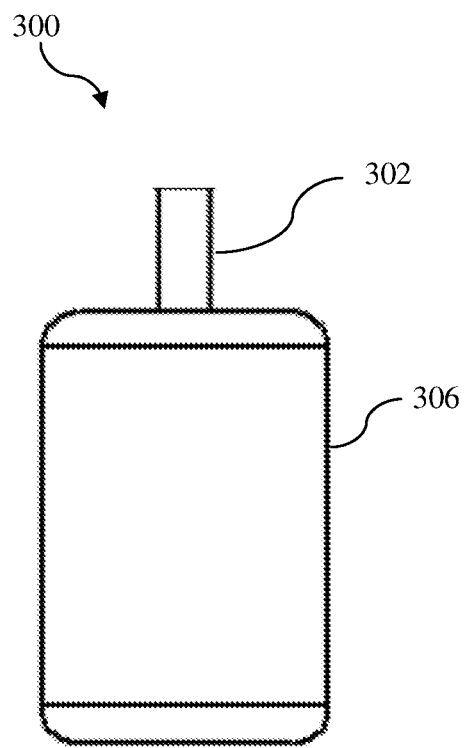
FIGS. 3A and 3B depict a schematic front view of a device for insertion into a body cavity according to an example embodiment of the present invention.
Figure 3B:
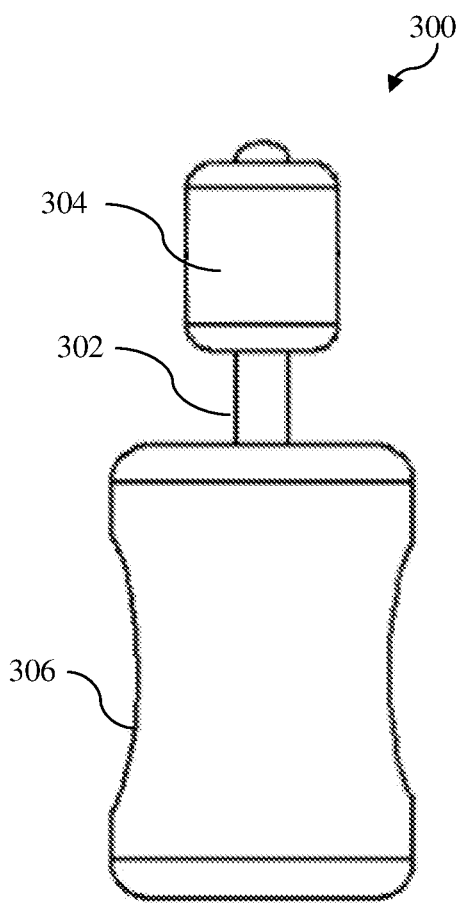

FIGS. 3A and 3B depict a schematic front view of a device 300 for insertion into a body cavity according to an example embodiment of the present invention. As shown, the device 300 comprises an insertion member 302 configured to be inserted into the body cavity, an expandable member 304 (not shown in FIG. 3A since the expandable member is stored within the insertion member 302) coupled to the insertion member 302 whereby the expandable member 304 is capable of being expanded to apply pressure onto tissue within the body cavity, and a first member 306 configured for storing a first endothermic reactant (e.g., fluid endothermic reactant) therein. In the example embodiment, the second member configured for storing a second endothermic reactant (e.g., solid or fluid endothermic reactant) is an internal compartment within the first member 306 and is thus not shown in the schematic front view of the device 300 in FIGS. 3A and 3B. FIG. 3A depicts the device 300 in a first state (e.g., an initial/original state before activation (before the expandable member 304 is inflated)) whereby the first member 306 has not yet been compressed to operate/activate the device 300. FIG. 3B depicts the device 300 in a second state (e.g., a compressed state (the expandable member 304 inflated)) after the first member 306 has been compressed to operate/activate the device 300 to inflate the expandable member 304. As illustrated in FIG. 3B, in the compressed state, the expandable member 304 expands from within the insertion member 302. Preferably, the expandable member 304 is expanded only after the insertion member 302 has been inserted into the body cavity at a desired location therein to, for example, provide physical compression or pressure to the hemorrhoids for treating the hemorrhoids (e.g., to tamponade the bleeding) in the anal canal. Although not shown in FIG. 3B, in the example embodiment, compressing the first member 306 reduces a volume within the first member 306, thereby forcing/pressuring the first endothermic reactant stored in the first member 306 to flow into the second member, via an opening in the second member, to cooperate with the second endothermic reactant stored in the second member to effect the endothermic reaction to generate the endothermic product. Furthermore, in the example embodiment, compressing the first member 306 will also cause the first endothermic reactant and/or the endothermic product to flow into the expandable member 304 through a channel in the insertion member 302, thereby resulting in the expansion of the expandable member 304 as illustrated in FIG. 3B.

Figure 4A:
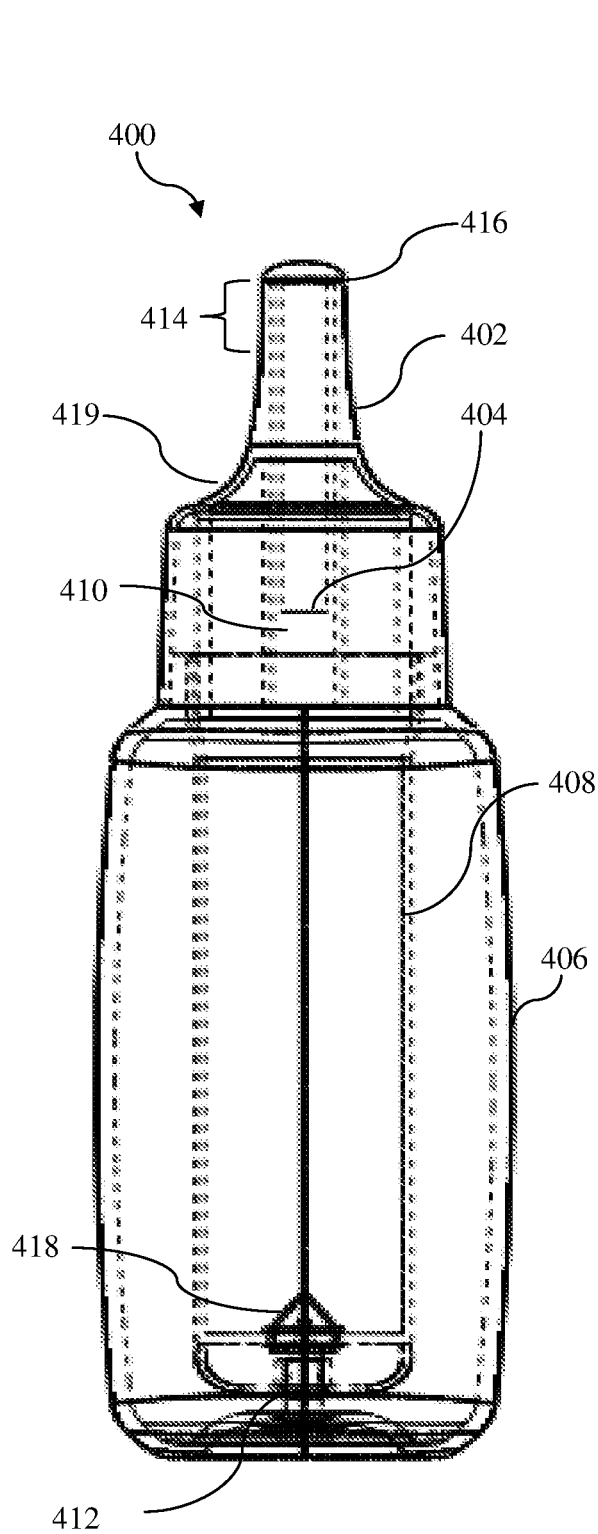
FIGS. 4A and 4B depict a schematic front view of a device for insertion into a body cavity according to an example embodiment of the present invention.
Figure 4B:
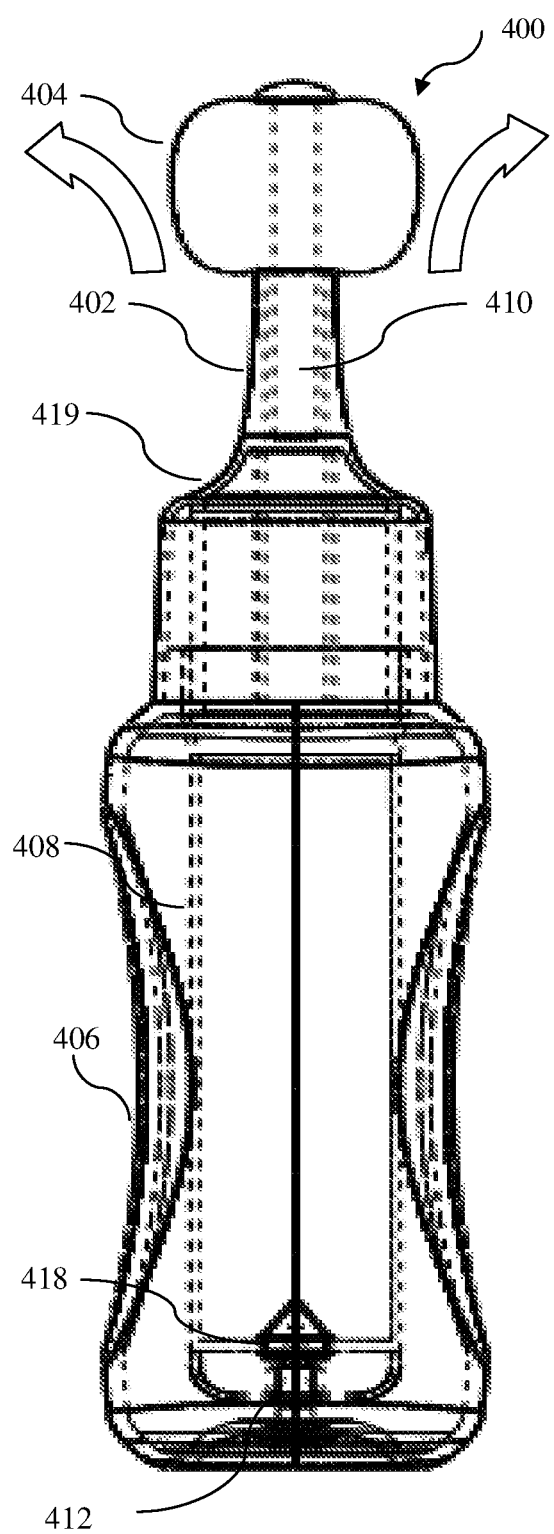

FIGS. 4A and 4B depict a schematic front view of a device 400 for insertion into a body cavity according to an example embodiment of the present invention. In various embodiments, the device 400 illustrated in FIGS. 4A and 4B may be considered to be a more detailed illustration of the device 300 shown in FIGS. 3A and 3B, with certain internal components better illustrated. As shown, the device 400 comprises an insertion member 402 configured to be inserted into the body cavity, an expandable member 404 coupled to the insertion member 402 whereby the expandable member 404 is capable of being expanded to apply pressure onto tissue within the body cavity, a first member 406 configured for storing a first endothermic reactant (e.g., fluid endothermic reactant) therein, and a second member 408 configured for storing a second endothermic reactant (e.g., solid or fluid endothermic reactant), separately from the first endothermic reactant.

FIG. 4A depicts the device 400 in a first state (e.g., an initial/original state before activation (before the expandable member is inflated)) whereby the first member 406 has not yet been compressed to operate/active the device 400. FIG. 4B depicts the device 400 in a second state (e.g., a compressed state (the expandable member inflated)) after the first member 306 has been compressed to operate the device 400. As illustrated in FIG. 4B, in the compressed state, the expandable member 404 expands from within the insertion member 402. Similar to the device 300, the expandable member 404 is preferably expanded only after the insertion member 402 has been inserted into the body cavity to at a desired location therein. As can be appreciated from FIG. 4B, in the example embodiment, compressing the first member 406 reduces a volume within the first member 406, thereby forcing/pressuring the first endothermic reactant stored in the first member 406 to flow into the second member 408, via an opening 412 in the second member 408 to cooperate with the second endothermic reactant stored in the second member 408 to effect the endothermic reaction to generate the endothermic product. Furthermore, in the example embodiment, compressing the first member 406 will also cause the first endothermic reactant and/or the endothermic product in the second member 408 to flow up via the resultant pressure and into the expandable member 404 through a channel 410 in the insertion member 402, thereby resulting in the expansion of the expandable member 404 as illustrated in FIG. 4B. As shown in FIGS. 4A and 4B, the insertion member 402 is coupled to the first member 406 such that the channel 410 of the insertion member 402 establishes fluid communication with the second member 408 for receiving the first endothermic reactant and/or the endothermic product from the second member 408.

As shown in FIGS. 4A and 4B, in the example embodiment, the first member 406 may be referred to as a reservoir (e.g., compressible bottle/container) and the second member is an internal compartment 408 (e.g., inflexible/non-compressible) located within the reservoir member 406. In this regard, the second member 408 comprises an opening 412 for receiving the first endothermic reactant from the reservoir member 406. For example, the opening 412 may be located at a bottom portion of the second member 408 as illustrated in FIGS. 4A and 4B. Various members/components of the device 400 will be described in more details later according to various embodiments of the present invention.

The exemplary devices 300, 400 described with reference to FIGS. 3 and 4 may show the first member 206 configured in the form of a bottle/container, such as a compressible/squeezable bottle. However, it will be appreciated to a person skilled in the art that the first member 206 can be configured in any form or shape as long as the first member is suitable/capable of storing/holding fluid (in particular, liquid) therein. For example, the first member 206 may instead be in the form of a flexible container bag, such as a foil bag.

FIGS. 5A and 5B depict a schematic front view of a device 500 for insertion into a body cavity according to an example embodiment of the present invention. As shown, the device 500 comprises an insertion member 502 configured to be inserted into the body cavity, an expandable member 504 (not shown in FIG. 5A since the expandable member is stored within the insertion member 502) coupled to the insertion member 502 whereby the expandable member 304 is capable of being expanded to apply pressure onto tissue within the body cavity, and a first member 506 configured for storing a first endothermic reactant (e.g., solid or fluid endothermic reactant) therein. As shown in FIGS. 5A and 5B, in the example embodiment, the first member 506 is in the form of a flexible container bag. FIG. 5C depicts a schematic cross-sectional view of the device 500. As shown in FIG. 5C, the device 500 further comprises a second member 508 configured for storing a second endothermic reactant (e.g., fluid endothermic reactant) therein, and the second member 508 is located within the first member 506.

FIG. 5A depicts the device 500 in a first state (e.g., an initial/original state before activation (before the expandable member is inflated)) whereby the first member 506 and the second member 508 have not yet been compressed to operate/activate the device 500. FIG. 5B depicts the device 500 in a second state (e.g., a compressed state (the expandable member inflated)) after the first member 506 and the second member 508 have been compressed to operate/activate the device 500. As illustrated in FIG. 5B, in the compressed state, the expandable member 504 expands from within the insertion member 502. As can be appreciated from FIG. 5C, in the example embodiment, compressing the first member 506 at a region where the second member 508 is located would also compress the second member 508, thereby reduces a volume within the second member 506 and causes (e.g., forces/pressures) the second endothermic reactant stored in the second member 508 to flow out of the second member 508 and into the first member 506 to cooperate or mix with the first endothermic reactant stored in the first member 506 to effect the endothermic reaction to generate the endothermic product. Furthermore, in the example embodiment, compressing the first and second members will cause the second endothermic reactant and/or the endothermic product to flow into the expandable member 504 through a channel 510 in the insertion member 502, thereby resulting in the expansion of the expandable member 504 as illustrated in FIG. 5B.

In the example embodiment, the insertion member 502 is coupled to the first member 506 and extends into the first member 506 such that the channel 510 of the insertion member 502 establishes fluid communication with the first member 506. As shown in FIG. 5C, the insertion member 502 may comprise a valve 509 at an end portion thereof within the first member 506 and in a first state (e.g., operating state) is configured to provide one-directional fluid flow through the valve 509 from the first member 506 to the channel 510 of the insertion member 502. The valve 509, in the first state, may thus function to prevent fluid in the channel and/or the expandable member 504 to flow back into the first member 506, thus maintaining the fluid in the expandable member 504 for maintaining the expandable member 504 in the expanded/inflated state.

Figure 5D:
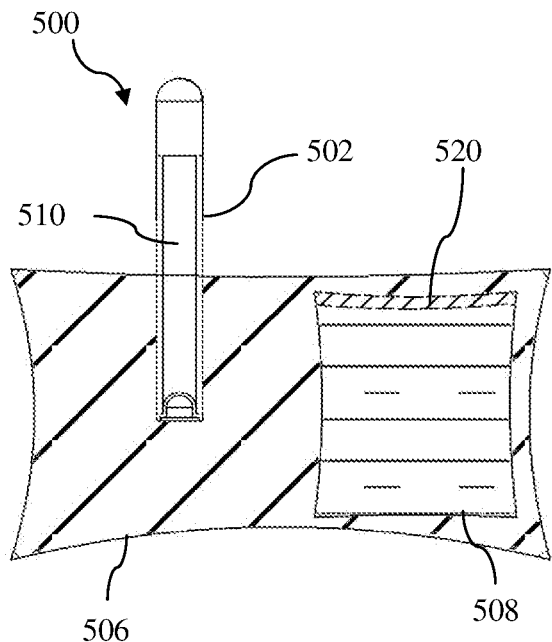
FIGS. 5D to 5I depict schematic cross-sectional view of the device shown in FIGS. 5A and 5B at various states according to various embodiments of the present invention.
Figure 5E:
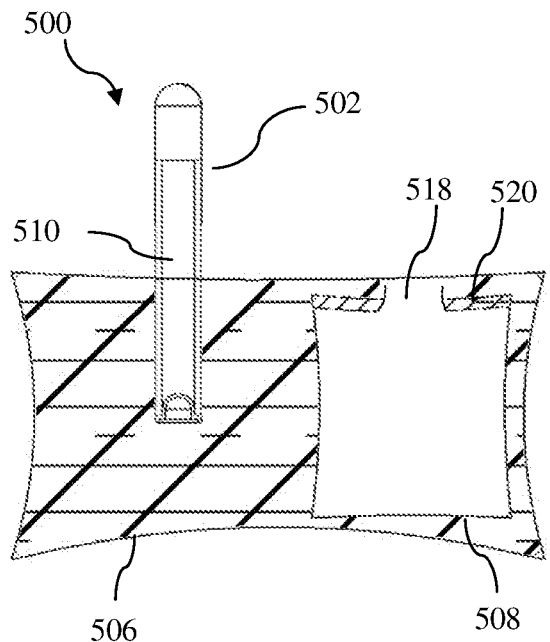
Figure 5F:
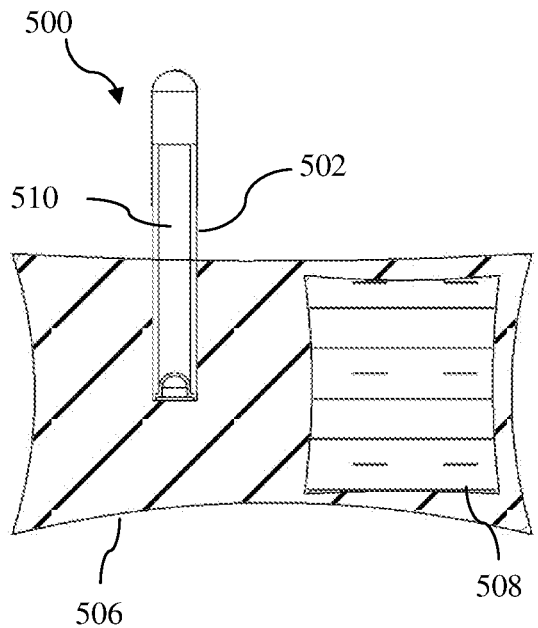
Figure 5G:
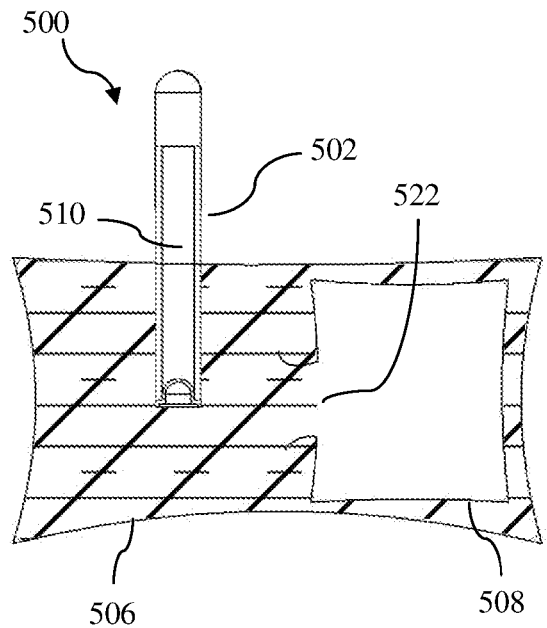
Figure 5H:
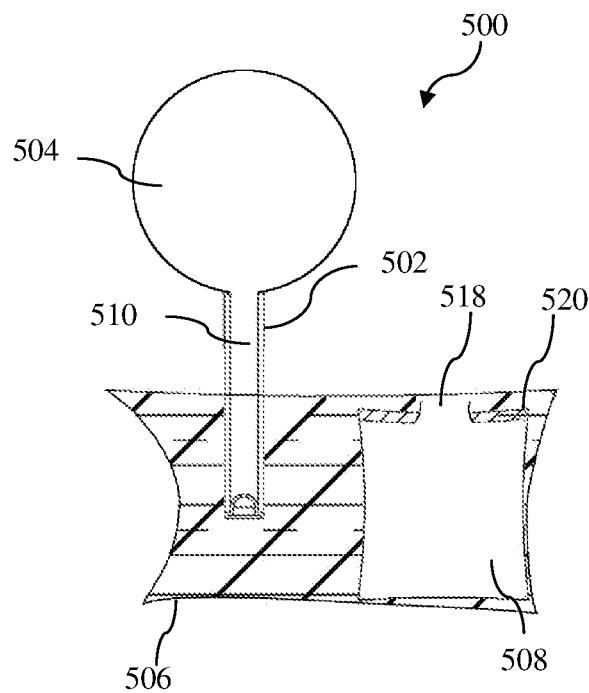
Figure 5I:
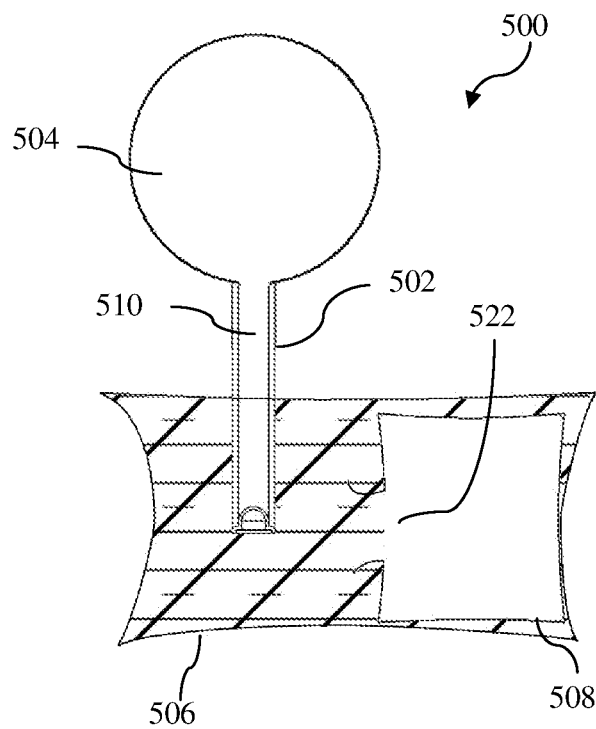

In various embodiments, the second member 508 may comprise an opening 518 sealed by a separating member/membrane 520 as illustrated in FIGS. 5D and 5E, or the second member 508 may constitute a separating member/membrane as illustrated in FIGS. 5F and 5G (i.e., the second member itself is the separating member/membrane). In this regard, the separating member/membrane is configured to, in a first state (e.g., an initial/original state before the expandable member 504 is inflated), block the first and second endothermic reactants from cooperating and, in a second state (e.g., in a compressed state after compressing the first and second members such that the separating member is broken), allow the first and second endothermic reactants to cooperate to effect the endothermic reaction. FIGS. 5D and 5E depict a schematic cross-sectional view of the device 500 in the first state and the second state, respectively. The first member 506 has stored therein the first endothermic reactant (shaded by diagonal lines) and the second member 508 has stored therein the second endothermic reactant (shaded by horizontal lines). It will be appreciated that the shaded region/section is for illustration purposes only and for example does not require the first member 506 and/or the second member 508 to be completely filled up with the respective endothermic reactant.

In the embodiment of FIGS. 5D and 5E, the separating membrane 520 is configured to seal an opening 518 of the second member 508. The separating membrane 520 (e.g., breakable or frangible) may be configured to break upon subjected to an applied pressure exceeding a certain/predetermined threshold from the fluid (second endothermic reactant) contained in the second member 508 when the second member 508 is compressed. By way of examples only and without limitation, the separating membrane may be made of laminated metal foils such as aluminum foils, or polymers such as polyvinyl chloride (PVC), ethylene-vinyl acetate (EVA), polypropylene, and/or polyethylene. As illustrated in FIG. 5E, once the separating membrane is broken, the second endothermic reactant contained in the second member 508 may then flow out of the second member 508 through the opening 518 and into the first member 506 to cooperate with the first endothermic reactant to effect the endothermic reaction.

In the embodiment of FIGS. 5F and 5G, the second member 508 constitutes or is made of the separating member, such as a breakable or frangible bag. In particular, the second member 508 is configured to be breakable at one or more portions 522 (e.g., random rupture) thereof upon being subjected to an applied pressure exceeding a certain/predetermined threshold from the fluid (second endothermic reactant) contained in the second member 508 when the second member 508 is compressed. By way of examples only and without limitation, the separating membrane may be made of laminated metal foils such as aluminum foils, or polymers such as polyvinyl chloride (PVC), ethylene-vinyl acetate (EVA), polypropylene, and/or polyethylene. Similarly, as illustrated in FIG. 5G, once the second member 508 is broken, the second endothermic reactant contained in the second member 508 may then flow out of the second member 508 through the broken/ruptured portion 522 and into the first member 506 to cooperating with the first endothermic reactant to effect the endothermic reaction.

In various embodiments, when the first and second members 506, 508 are compressed to cause the first and second endothermic reactants to cooperate to effect an endothermic reaction, such applied pressure is sufficient to also inflate the expandable member 504. In various other embodiments, the first and second members 506, 508 may be compressed to cause the first and second endothermic reactants to cooperate to effect an endothermic reaction without causing the expandable member 504 to inflate as shown in FIGS. 5E and 5G as a step. In this regard, for example, the insertion member 502 may have a removable lid or cap (not shown) releasably secured to a distal end portion of the insertion member 502 where the expandable member 504 is configured to expand out from as a safety feature to prevent the accidental inflation of the expandable member 504. Then, as a subsequent step, the lid or cap may be removed and then the insertion member 502 inserted in the body cavity to perform the treatment. The first member 506 (now containing the endothermic product) may then be compressed further to pressure the endothermic product to flow up the channel 510 to inflate the expandable member 504.

Various members/components of the example devices 300, 400, 500 described above with reference to FIGS. 3 to 5 will now be described hereinafter in more details according to various embodiments of the present invention by way of examples only and not limitations. Unless stated otherwise or clearly incompatible, the members/components described are applicable to the corresponding members/components of each of the example devices 300, 400, 500 described herein.

Insertion Member

In various embodiments, the insertion member is configured for simple and safe insertion into the body cavity, and in particular, the anal canal. In an example embodiment, the insertion member may have an elongated structure suitable for insertion into the body cavity, such as a column or shaft structure. As an example and without limitation, the insertion member may be a circular column having a diameter in the range of about 3 mm to about 15 mm, and a length (e.g., amount protruding from the first member) of about 1 cm to about 5 cm. It will be appreciated that the dimensions of the insertion member may be configured as appropriate to allow easy insertion into the anus and such that its distal end region proximal can be located in the vicinity of or adjacent to the hemorrhoids in the anal canal after insertion. For example, the insertion member may also have a curved or rounded end to allow for easy/comfortable insertion into the anal canal. As another example, the insertion member may also be tapered in shape, with the initial entry portion (distal end portion) of the insertion member having a smaller cross sectional area than the proximal end portion (adjacent the first member) of the insertion member.

Figure 6A:
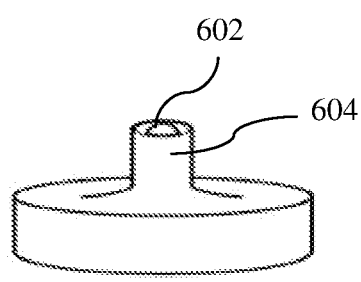
FIG. 6 depicts a schematic front view of an extendable insertion member according to an example embodiment of the present invention.
Figure 6B:
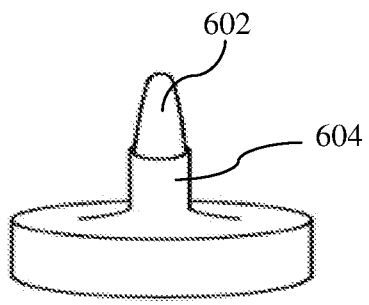

In various embodiments, the insertion member is configured so as to be extendable. For example, the insertion member may be extendable via a telescoping mechanism as illustrated in FIGS. 6A and 6B. In this regard, the insertion member may comprise at least an inner component 602 and an outer component 604. For example, the outer component 604 may be configured to have an internal diameter and length that is sufficient to house and retain the inner component 602 prior to the inner component 602 being deployed. The inner component 602 may be configured to have an outer diameter that is smaller (e.g., slightly smaller such that the inner component 602 can closely fit (snugly) within the outer component 604) than the inner diameter of the outer component 604. Accordingly, the insertion member may have an initial length defined by the outer component 604 (e.g., about 2 cm or less) and can be extended in length (e.g. to about 5 cm or less) when the inner component 602 is deployed. The extension of length (telescoping mechanism) can be initiated by various techniques such as, but not limited to, auto-deployment as the insertion member is inserted into the anal canal (e.g., the telescope mechanism may be configured to be pressure sensitive and deployed as pressure is applied thereto during insertion, or compressing the first member may result in triggering the telescope mechanism to deploy), an actuating mechanism such as a button or a switch, or any other appropriate/suitable techniques known in the art. In an embodiment, the insertion member may include an overlying protective sheath to protect the tissue from being cut or clipped in between the inner and outer components 602, 604 during insertion of the insertion member into the anal canal.

In various embodiments, the insertion member comprises a channel extending along its longitudinal axis for receiving the first endothermic reactant and/or the endothermic product and outputting to the expandable member coupled thereto. As an example, referring to the device 400 shown in FIGS. 4A and 4B, the insertion member 402 comprises a channel 410 extending along its longitudinal axis. Furthermore, a distal end region/portion 414 of the insertion member 402 may comprise an opening 416 arranged for allowing the expandable member stored within the insertion member 402 to expand through, such as illustrated in FIG. 4B (see also FIG. 5B).

In various embodiments, a removable lid or cap (not shown) may be releasably secured to a distal end portion of the insertion member where the expandable member is configured to expand out from as a safety feature to prevent the accidental inflation of the expandable member. The lid or cap may be removed prior to inserting the insertion member in the body cavity to perform the treatment.

Stopper Member

In various embodiments, a stopper member may be provided at a predetermined location along the insertion member, such as at or near the proximal end of the insertion member. The stopper member may be configured to have a cross-section larger than the insertion member and the body cavity so as to function as a safety component. For example, the stopper member may function to prevent the insertion member from being inserted into the body cavity further than intended, and would also prevent the whole device (in the case if the first member is sufficiently small or flexible) from being entirely inserted/slipped into the body cavity during treatment. The stopper member may be configured to have various shapes as appropriate such as a planar or circular shape so as to comfortably rest in between the anal cleft. The stopper member may thus allow safe and accurate insertion of the insertion member into the body cavity, as well as making the device user-friendly such as enabling self-insertion.

In various embodiments, the stopper member may be integrated with the insertion member such as illustrated in FIGS. 4A and 4B. In particular, in the embodiment of FIGS. 4A and 4B, the stopper member 419 is realized by a wide portion of the insertion member 402 configured to have a cross-section larger than the insertion portion of the insertion member 402 and the body cavity so as to block the insertion member 402 from being inserted further than the wide portion. For example, the stopper member 419 may have a curved outer surface so as to comfortably rest in between the anal cleft when the insertion member 402 is inserted into the body cavity. In various embodiments, the stopper member 519 may be an overmold or fitment member arranged at a top or upper portion of the first member as illustrated in FIGS. 5A and 5B. In particular, in the embodiment of FIGS. 5A and 5B, as the first member 506 is flexible, such as a flexible container, the stopper member 519 is provided over the first member 506 to act as a stopper to prevent the device 500 from being inserted into the body cavity further than intended.

Expandable Member

In various embodiments, the expandable member is configured to be in a collapsed/deflated state during insertion of the insertion member into the anal canal. Once the insertion member is at a desired/correct position/location inside the anal canal, the expansion of the expandable member may be initiated to expand the expandable member so as to create a constant pressure on the hemorrhoidal tissue, for example, to apply tamponade to the bleeding blood vessel. In various embodiments, the expandable member may also be referred to as a pressure application member or simply a balloon.

In various embodiments, the expandable member is coupled to the insertion member at a distal end region of the insertion member. As an example, FIG. 4A illustrates the expandable member 404 coupled to the insertion member 402 at a distal end region 414 of the insertion member 402. Therefore, the expandable member 414 is configured to expand from within the insertion member 402 at the distal end region 414 of the insertion member 402.

Figure 7:
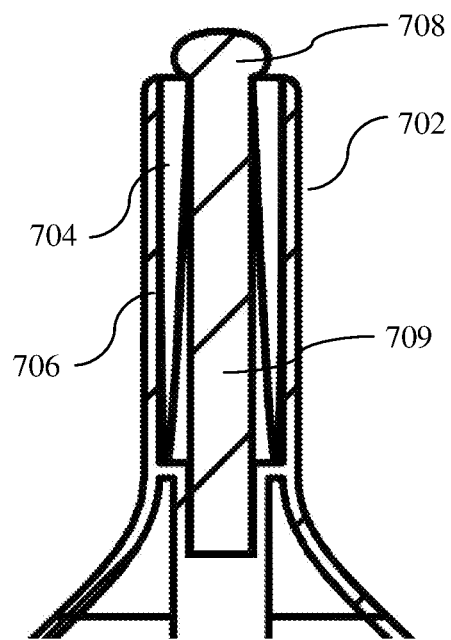
FIG. 7 depicts a schematic cross-sectional view of an insertion member having stored therein an expandable member in a collapsed/deflated state according to an example embodiment of the present invention.

As an exemplary illustration, FIG. 7 depicts a schematic drawing of an insertion member 702 having an expandable member 704 stored within an internal space or channel 706 therein in a collapsed/deflated state according to various embodiments of the present invention before being expanded. With such a configuration, the insertion member 702 can be kept as compact as possible and facilitates insertion into the body cavity without the expandable member 704 capable of obstructing. For example, after the insertion member 702 has been inserted at the desired/correction location within the body cavity, the expandable member 704 may then expand from within the channel 706 to apply pressure to, for example, the hemorrhoids within the anal canal to contact the tissue and tamponade the bleeding by, for example, the fluid endothermic reactant and/or the endothermic product received in the expandable member 704.

Various forms/configurations of the expandable member and various mechanism for expanding the expandable member will now be described according to various example embodiments of the present invention. It will be appreciated by a person skilled in the art that the present invention are not limited to such example embodiments, and various other forms/configurations are also within the scope of the present invention as long as the expandable member is capable of being expanded from a compacted/collapsed state to an expanded state to apply pressure onto tissue within the body cavity.

Figure 8A:
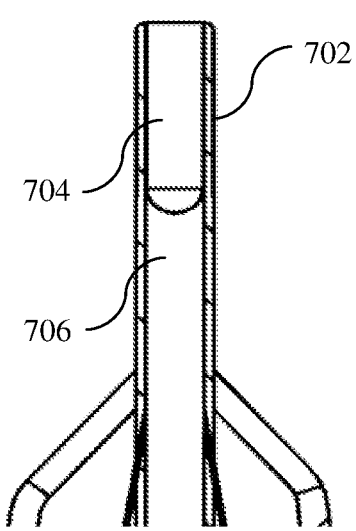
FIGS. 8A and 8B depict a schematic cross-sectional view of an insertion member having stored therein an expandable member in a collapsed/deflated stated according to another example embodiment of the present invention.
Figure 8B:
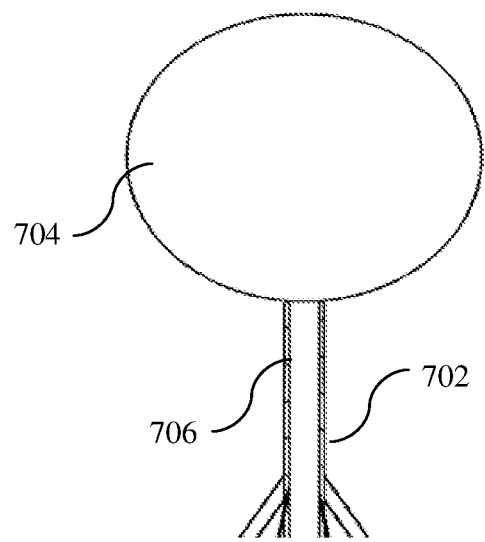

According to various example embodiments, a balloon-like expansion mechanism is provided for the expandable member. The expandable member (balloon component) is configured to be collapsed and deflated during insertion of the device into the anal canal. Once at the correct/desired position, the inflation of the expandable member will be initiated to create constant pressure on the hemorrhoidal tissue. As described hereinbefore, the expandable member may be folded or compacted within an internal space 706 of the insertion member 702. FIG. 8A depicts another schematic drawing of the insertion member having the expandable member 704 coupled thereto and stored in the channel 706 therein. Upon the compression of the compressible first member (reservoir member), fluid volume from the first member enters (e.g., fills up) the expandable member 704 and causes the expansion of the expandable member 704. The fluid also causes the expandable member 704 to slide out of the insertion member 702 as illustrated in FIG. 8B.

In various embodiments, a distal end region/portion of the expandable member may comprise a rigid/stiff cap structure/feature. An exemplary cap structure 708 having a shaft 709 is illustrated in FIG. 7. The cap structure may function to minimize the expansion of the expansion member in a longitudinal direction of the expandable member (e.g., longitudinal direction of the anal canal) when there is an increase in pressure exerted from the anal canal on the expandable member. The cap structure may also function to provide greater lateral expansion of the expandable member than longitudinal expansion of the expandable member so as to apply greater pressure on the hemorrhoidal tissues on the side wall of the anal canal.

In various embodiments, the expandable member may be designed/configured to deform (such as into a non-spherical or irregular shape) when the pressure exerted on the expandable member increases beyond a particular or predetermined threshold value.

In various embodiments, the expandable member comprises an external or outer layer made of a soft material, such as but not limited to, foam, cotton or cellulose for cleaning the anal canal when the device is used.

In various embodiments, the expandable member has a layer of therapeutic substance disposed on its outer surface for delivering the therapeutic substance to the tissue within the body cavity (e.g., anal canal). Accordingly, therapeutic drugs may be delivered to within the body cavity to, for example, treat inflamed tissues. The layer of therapeutic drugs may configured in a mesh or film form and may be separable from the expandable member such that the layer may remain/reside on the side wall of the body cavity even after the expandable member/insertion member has been removed. Such an expandable member will be described later with reference to FIG. 20B according to an example embodiment of the present invention.

In various embodiments, at least a portion of the expandable member comprises pores configured for allowing fluid (e.g., therapeutic substance) in the expandable member to discharge (seep out) through the pores for delivery of the therapeutic substance to the tissue within the body cavity. For example, the fluid (in particular, liquid) may then irrigate the anal region for various purposes, such as to enable better bowel movement. The liquid may also be therapeutic in nature for various types of treatment as desired/appropriate. Such an expandable member will be described later with reference to FIG. 20A according to an example embodiment of the present invention.

In various embodiments, the expandable member comprises a plurality of compartments. For example, one of the compartments may be configured to receive the first or second endothermic reactant (fluid endothermic reactant) and/or the endothermic product to, for example, expand the expandable member and/or to deliver a cold therapy, while another one or more of the compartments may be configured to receive or have stored therein fluid (in particular, liquid) for delivering irrigation and/or therapeutic substance to the anal region through the pores of such compartment(s). Such an expandable member will be described later with reference to FIGS. 20C and 20D according to example embodiments of the present invention.

In various embodiments, the expandable member is coated with irrigation and/or therapeutic substance. Accordingly, the irrigation substance may be delivered within the body cavity and/or the therapeutic substance may be applied to tissues within the body cavity after the insertion member is inserted and the expandable member inflated within the body cavity.

Figure 9:
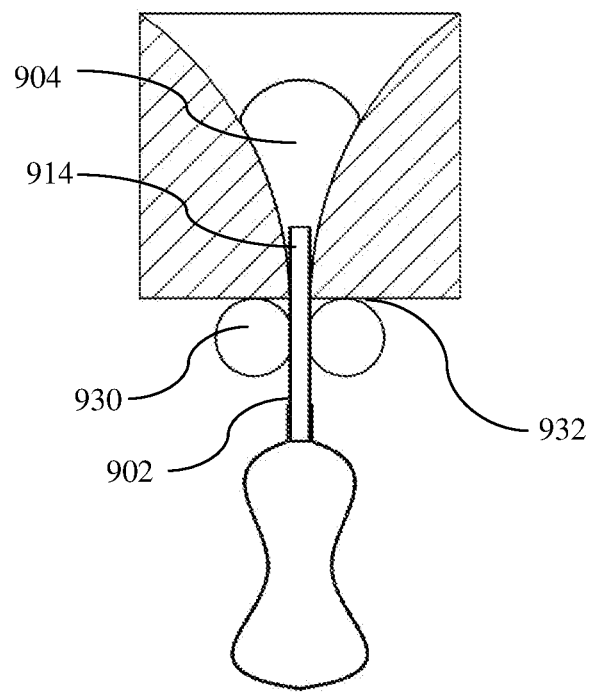
FIG. 9 depicts a device comprises an external expandable member coupled to the insertion member according to various embodiments of the present invention.

FIG. 9 depicts a device comprises an external expandable member 930 coupled to the insertion member 902 at a predetermined distance from the distal end region 914 according to various embodiments of the present invention. In this regard, the external expandable member 930 is capable of being expanded to apply pressure onto an external region/area 932 of the body cavity. As shown, the external expandable member 930 may be additional to the expandable member (internal expandable member) 904 configured to be inserted within the body cavity, and the external expandable member 930 is configured to be located outside/external of the body cavity that is being treated during treatment. For example, the external expandable member 930 may also deliver cold therapy to the external area 932 of the body cavity. The external expandable member 930 may further act to create a counter force for pulling the internal expandable member 904 as the external expandable member 930 is expanded. This would advantageously increase the pressure exerted on the tissue within the body cavity as shown in FIG. 9, thereby delivering an improved therapy/treatment. According to an embodiment, the predetermined distance from the distal end region 914 is determined based on a length of the insertion member 902 which is configured/intended to be inserted into the body cavity. For example, the predetermined distance may be determined such that the external expandable member 930 is able to expand onto an external region 932 of the body cavity with sufficient/desired pressure thereon after the insertion member 902 has been inserted into the body cavity at a desired location/position.

In various embodiments, the expandable member (or balloon member) may be made of one or a combination of different materials. In general, materials can be classified according to the compliance of the balloon member, namely non-compliant, semi-compliant or compliant balloons. Compliance correlates directly to the materials that the balloon member is made of. Non-compliant balloons have a higher burst pressure for a given profile. Its expanded diameter remains very close to its stated diameter and minimally expands further, even when inflated several atmospheric pressure (atm) above their nominal pressure. Compliant balloons are very flexible and elastic, such that they may expand beyond the diameter stated. Semi-compliant balloons may share the benefits of both the compliant and non-compliant balloons. These materials (or a combination of these materials) may be incorporated in the expandable member, and in various embodiments, strategically above the hemorrhoids in the anal canal to deliver the desired pressure to, for example, arrest and tamponade bleeding. By way of example only and without limitations, the expandable member can be made of materials that are elastic, semi-elastic or inelastic, and includes, but not limited to, polyurethanes, polydimethylsiloxanes, latex, vulcanized rubber, various combinations thereof or other polymers and copolymers that are bio-compatible.

In various embodiments, the balloon member may be configured to have a uniform thickness or unequal distribution of thickness (or stiffness) across its surface. A uniform thickness of the balloon member will allow for uniform expansion of the balloon in all directions (circumferentially/radially) to, for example, produce a substantially spherical shape. On the other hand, unequal thickness of the balloon member will result in unequal expansion radially (expand non-uniformly in a radial direction), with preferential and greater expansion at portions of the balloon member that are thinner (less stiff) in thickness. For example, configuring the balloon member to have a non-uniform thickness across its surface can allow greater pressure to be delivered to the desired/appropriate location(s) within the body cavity to improve treatment of the hemorrhoidal, such as improving the tamponade of the hemorrhoidal vessels.

In various embodiments, the surface of the balloon member may be configured to be smooth or corrugated/roughened in texture. For example, a smooth surface may provide equal distribution of the pressure onto the surface of opposing tissue contacted by the balloon member. On the other hand, as a corrugated surface does not provide even contact of the opposing tissue, the pressure will be unequally distributed onto the surface of opposing tissue with higher pressure on the surface portions making contact with the surface of the balloon member and lower pressure on surface portions not actually in contact with the surface of the balloon member. For example, a balloon member having a corrugated surface may allow for continuous perfusion of the tissue (especially in the low pressure areas) to allow blood perfusion to its microvasculature and reduce the risk of ischemia.

The balloon member may be configured to have various shapes/forms when expanded as appropriate or desired, for example, based on the intended or desired direction(s) in which the balloon member is to expand to apply pressure at appropriate or desired locations/portions of the tissue surface of the body cavity. By way of examples only and without limitation, the various shapes/forms include spherical shape, hemispherical shape, mushroom shape, clover shape, flower shape, and so on.

Figure 10A:
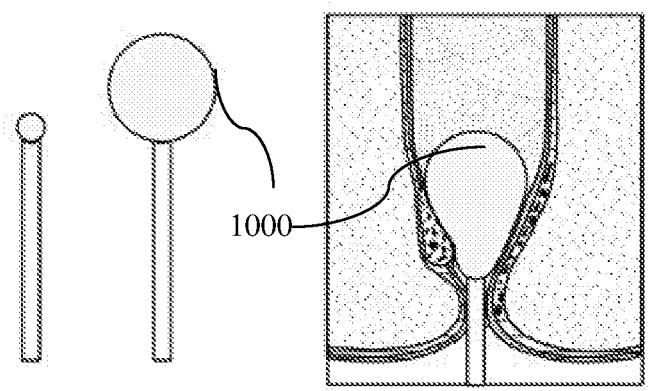
FIGS. 10A to 10E depict schematic drawings of various shapes/forms of the expandable member according to various embodiments of the present invention.
Figure 10B:
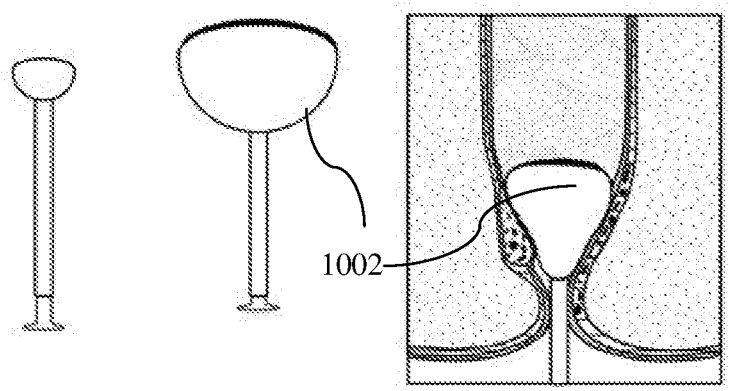
Figure 10C:
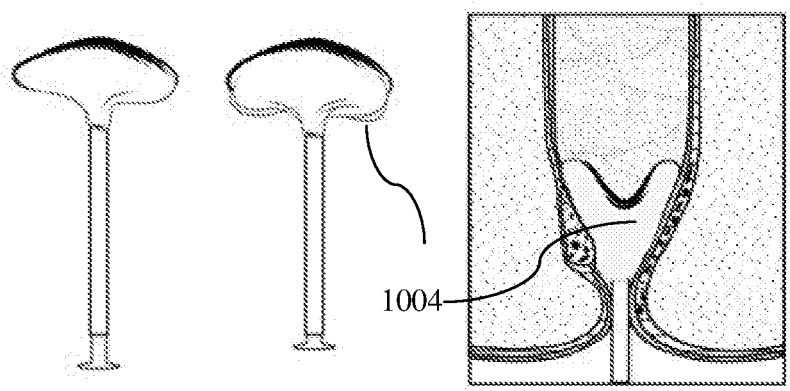
Figure 10D:
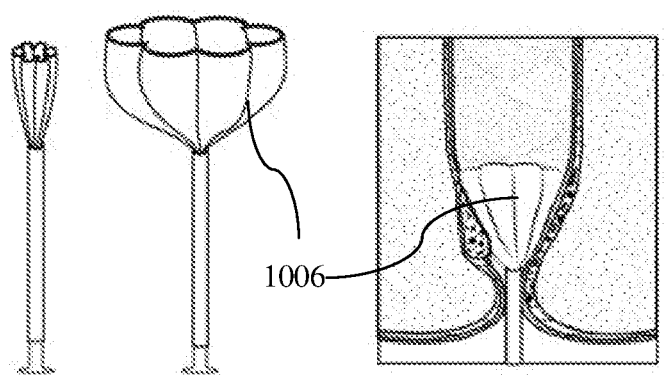
Figure 10E:
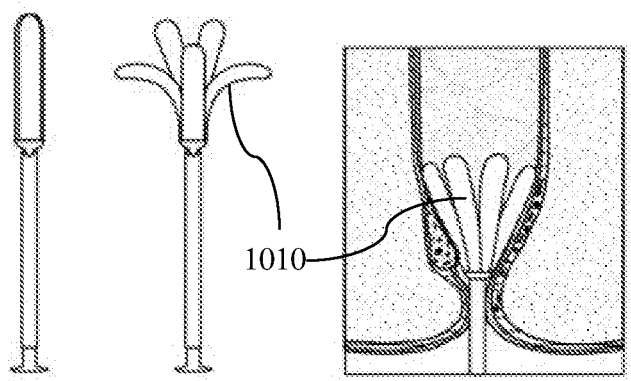

For illustration purposes only, FIG. 10A depicts a schematic drawing of a spherical-shaped balloon 1000 which, for example, may be used for delivering constant and even pressure by its spherical surface area on the underlying hemorrhoidal tissue and vessels when inflated as illustrated. FIG. 10B depicts a schematic drawing of a hemispherical-shaped balloon 1002 which, for example, may be used to deliver constant and even pressure by its spherical surface portion. FIG. 10C depicts a schematic drawing of a mushroom-shaped balloon 1004, which may be made of varying thickness or stiffness of material that can result in an unequal expansion of the balloon radially. For example, such a configuration can result in a greater expansion and higher pressures exerted on the underlying hemorrhoidal tissue and vessels at locations/portions of the balloon that is thinner in thickness or made of a less stiff material. The balloon may also be configured to have a clover shape, which may be used to target common/typical locations of hemorrhoids, such as at the 4, 7, 11 o'clock positions in the anal canal, where the 12 o'clock position is directed to the perineum. For example, such a configuration may be aimed to avoid constant circumferential pressure on the hemorrhoidal tissue to reduce risk of ischemia. FIG. 10D depicts a schematic drawing of a flower-shaped balloon 1006. For example, the balloon 1006 may open to have a flower-like shape comprising multiple compartments/bladders/columns (e.g., capable of receiving fluid to expand) that expand in an outward direction to create circumferential compression on any underlying hemorrhoidal tissue and vessels as illustrated in FIG. 10D. FIG. 10E depicts a schematic drawing of another type of flower-shaped balloon 1010, and in particular, configured to comprise a plurality of flower petals, each flower petal functioning as a separate compartment (e.g., capable of receiving fluid to expand) that expand in an outward direction to compress any underlying hemorrhoidal tissue as illustrated in FIG. 10E.

According to various example embodiments, a mechanical expansion mechanism is provided for the expandable member. Such an expandable member may be configured to provide compression and tamponade of the hemorrhoidal tissue and blood vessels via mechanical techniques. For example, after insertion into the anal canal at the correct position over the hemorrhoids, the expansion mechanism of the expandable member may be deployed, for example, by a mechanical action by the user or via an automated process directed by physical factors of the surrounding environment or anal canal anatomy, such as but not limited to, pressure differences within the anal canal.

In an example embodiment, the expandable member is made of a pre-formed or shape-memory material (such as, but not limited to, rubber or nitonol) contained within an external outer sheath. Once inserted in the correct/desired position over the hemorrhoidal tissue/vessel, the outer sheath is removed and the underlying expandable member may then expand into its pre-formed/original shape to deliver pressure over the hemorrhoidal tissue and vessels. FIG. 11A depicts a schematic drawing of the expandable member 1150 in the form of nitinol wire initially contained within the external outer sheath 1152. After the external outer sheath 1152 is adjusted downwards, the nitinol wire is released and expands outwards to deliver pressure to the hemorrhoidals as it reverts back to its pre-formed/original shape. FIG. 11B depicts a schematic drawing of the expandable member 1160 in the form of compressed wire initially contained with the external outer sheath 1152. Similar to the expandable member 1150 described with reference to FIG. 11A, after the external outer sheath 1152 is adjusted downwards, the compressed wire is released and expands outwards to deliver pressure to the hemorrhoidals as it reverts back to its pre-formed/original shape. FIG. 11C depicts a schematic drawing of the expandable member 1170 in the form of a sponge contained with the external outer sheath 1152. Similarly, after the outer sheath 1152 is adjusted downwards, the sponge is released and expands outwards to deliver pressure to the hemorrhoidals as it reverts back to its pre-formed/original shape.

Figure 12:
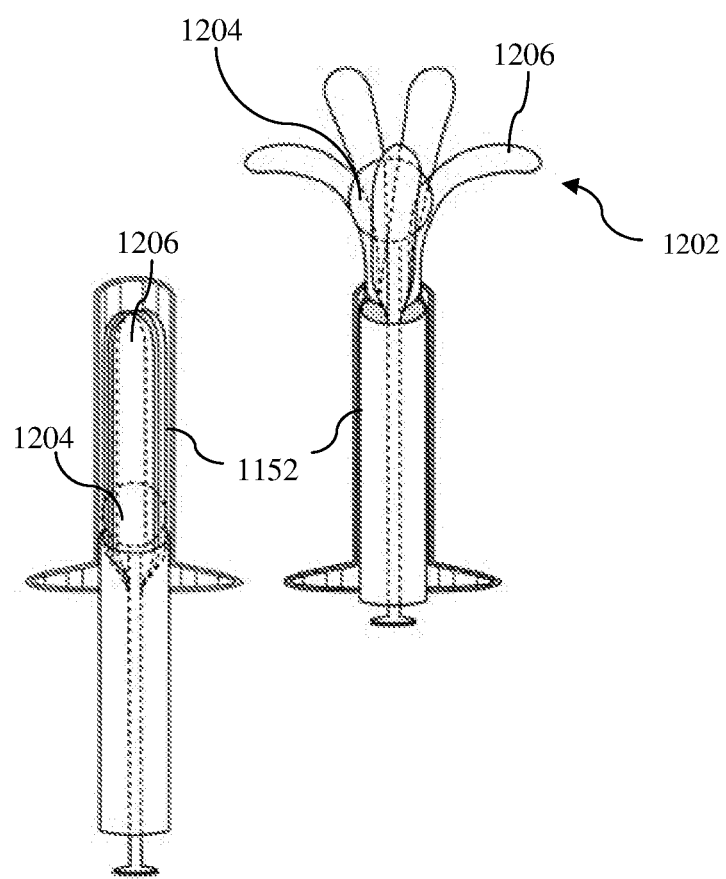
FIG. 12 depicts a schematic drawing of a device configured with a combination of a balloon-type expansion mechanism and a mechanical expansion mechanism.

According to various embodiments, the balloon-type expansion mechanism and the mechanical expansion mechanism may be combined. FIG. 12 depicts a schematic drawing of an expandable member 1202 comprising a balloon member 1204 and a movable/adjustable solid member 1206. As shown in FIG. 12, the solid member 1206 may be in the form of a plurality of struts (strut arrangement) and the strut arrangement, together with the deflated balloon member 1204 therein, is initially compressed within an outer sheath 1152. Once inserted in the correct/desired position over the hemorrhoidal tissue/vessel, the outer sheath 1152 is removed and the inflation/expansion of the balloon member 1204 would then expand the strut arrangement 1206 in an outwardly direction to mechanically apply pressure onto the tissue within the body cavity, such as to tamponade the underlying hemorrhoidal vessel and tissues.

First and Second Members

According to various embodiments, the first member is a reservoir member configured to be capable of containing fluid, such as, for storing/holding the first endothermic reactant therein. For example, the first endothermic reactant may be in the fluid/liquid form as, for example, described in the example embodiments of FIGS. 3 and 4, or the first endothermic reactant may be in the solid form (e.g., urea salt) in the example embodiment of FIG. 5. The second member is configured for storing/holding the second endothermic reactant therein and is preferably located within the first member as, for example, described in the example embodiments of FIGS. 3 to 5. For example, the second endothermic reactant may be in the solid form (e.g., urea salt) as, for example, described in the example embodiments of FIGS. 3 and 4, or the second endothermic reactant may be in the fluid/liquid form as, for example, described in example embodiment of FIG. 5. As mentioned hereinbefore, it will be appreciated to a person skilled in the art that a first endothermic reactant and a second endothermic reactant cooperating to effect an endothermic reaction is not limited to involving only the first and second endothermic reactants, and can include additional endothermic reactant(s) as long as the endothermic reaction involves at least the first and second endothermic reactants. Therefore, it will also be appreciated to a person skilled in the art that the present invention is not limited to a first member and a second member for storing a first endothermic reactant and a second endothermic reactant respectively, and that additional member(s) for storing additional endothermic reactant(s) respectively may be included in the device, for example, in the case of the endothermic reaction involving additional endothermic reactant(s).

In various embodiments, the upper or proximal portion of first member may be configured to sit/rest comfortably at the anal verge and may function as a safety mechanism (stopper) to prevent excessive insertion of the device into the anal canal. The cross-sectional area of the upper portion may have a substantially triangular/conical shape adapted to fit comfortably in the gluteal cleft and may also function to provide directional information for the users to insert the device in the correct direction (e.g., tip portion to the front and base portion to the back).

The first member is configured to be compressible (e.g., upon application of compression pressure by the user) to cause the first member to deform. In this regard, compressing the first member would reduce a volume within the first member thereby forcing the first endothermic reactant stored in the first member and/or the second endothermic reactant stored in the second member to flow to cooperate with each other to effect the endothermic reaction to generate the endothermic product. That is, the movement of the first endothermic reactant and/or the second endothermic reactant to cooperate with each other can trigger the endothermic reaction to create the instant cold therapy. Preferably, the first member is made of a flexible/deformable material to facilitate/enable the compression of the first member by the user, such as but not limited to, santoprene thermoplastic volcanizates (TPVs), ethylene-vinyl acetate (EVA), flexible polyvinyl chloride (flexible PVC).

In various embodiments, the compressible first member is filled with one of the endothermic reactants (e.g., the first endothermic reactant). In various embodiments, the compressible first member may be partially filled to enable the compression of the first member at a lower applied pressure (e.g., squeezing pressure). Furthermore, in various embodiments, the compressible first member may have negative pressure. For example, the negative pressure would enable faster deflation of the expandable member when deflating the expandable member.

The second member may be a rigid and/or non-compressible internal chamber as, for example, shown in the example embodiment of FIG. 4, or second member may be a flexible and/or compressible internal compartment (e.g., flexible bag) as, for example, shown in the example embodiment of FIG. 5. As described hereinbefore in the example embodiment of FIG. 5, the second member 508 may comprise an opening 518 sealed by a separating member/membrane 520 as illustrated in FIGS. 5D and 5E, or the second member 508 may constitute a separating member/membrane as illustrated in FIGS. 5F and 5G.

In various embodiments, one or more second members (one or more internal compartments or chambers) are provided within the first member. In particular, at least one internal compartment stores/holds a second endothermic reactant therein. In various embodiments, the internal compartment is configured to be in fluid communication with the expandable member. For example, referring to the device 400 shown in FIGS. 4A and 4B, the first member 406 is a reservoir and the second member 408 is an internal compartment within the reservoir. Furthermore, the second member 408 comprises an opening 412 for receiving the first endothermic reactant from the first member 406. With this configuration, compressing the first member 406 would reduce a volume within the first member 406 thereby forcing the first endothermic reactant (liquid form) stored in the first member 406 to flow into the second member 408 to cooperate with the second endothermic reactant (e.g., solid form) stored in the second member 406 to effect the endothermic reaction to generate the endothermic product. In such embodiments, the endothermic reaction occurs in the second member 408 as the first endothermic reactant flows in to cooperate with the second endothermic reactant present in the second member 408, and as the expandable member 404 is in fluid communication with the second member 408 via a fluid channel 410 in the insertion member 402, the first endothermic reactant and/or the endothermic product would flow from the second member 408 to the expandable member 404, thereby inflating the expandable member 404 as illustrated in FIG. 4B. Furthermore, with this configuration, the compressible first member 406 surrounds the internal chamber and would thus advantageously be able to act as an insulator for the endothermic reaction occurring in the second member 408. Therefore, for example, the user's hand would not be subjected to a cold effect while holding the first member 406 during treatment, and would thus be able to hold the device 400 for a longer period of time if necessary.

On the other hand, referring to the device 500 shown in FIG. 5, the second member 508 is an internal compartment (e.g., flexible container/bag) within the first member (e.g., flexible container/bag) 506. Furthermore, as described hereinbefore, the second member 508 may comprise an opening 518 sealed by a separating member/membrane 520 as illustrated in FIGS. 5D and 5E, or the second member 508 may constitute a separating member/membrane as illustrated in FIGS. 5F and 5G. With this configuration, compressing the first member 506 at a region where the second member is located would compress the second member, thereby reduces a volume within the second member 508 and causes the separating member to break to allow the second endothermic reactant (e.g., liquid form) stored in the second member 508 to flow out of the second member 508 and into the first member 506 to cooperate with the first endothermic reactant (e.g., solid form) stored in the first member 506 to effect the endothermic reaction. In such embodiments, the endothermic reaction occurs in the first member 506 as the second endothermic reactant flows in to cooperate with the first endothermic reactant present in the first member 506, and as the expandable member 504 is in fluid communication with the first member 506 via a fluid channel 510 in the insertion member 502, the first endothermic reactant and/or the endothermic product would flow from the first member 506 to the expandable member 504, thereby inflating the expandable member 504 as illustrated in FIG. 5B.

In various embodiments, at least one second member stores/holds irrigation and/or therapeutic substance for delivery within the anal canal, such as but not limited to, saline or drugs.

Valve

In various embodiments, such as in the example embodiments of FIGS. 3 and 4, a valve may be arranged between the first member and the second member (i.e., in the opening or fluid communication path between the first member and the second member) for controlling fluid flow therebetween. In various embodiments, the valve may be pressure sensitive. For example, as illustrated in FIGS. 4A and 4B, a valve 418 is arranged at an opening 412 of the second member 408 configured for receiving the first endothermic reactant from the reservoir member such that the valve 418 is capable of controlling fluid flow therebetween. In particular, the valve 418 is configured to, in a first state (e.g., when the first member 406 is compressed to perform treatment), provide one-directional fluid flow through the valve 418 from the first member 406 to the second member 408. As the valve 418 is operable as a one-way valve when the first member 406 is compressed to perform treatment, fluid in the second member 408 (e.g., the first endothermic reactant that has flowed in) is prevented from flowing back into the first member 406, thereby limiting the endothermic reaction to the second member 408 and the expandable member 404. That is, when the first endothermic reactant from the compressible first member 406 mixes with the endothermic reactant in the second member 408, the mixture does not flow back into the first member 406. This advantageously enables the cold therapy from the endothermic reaction to last longer as the endothermic reaction mixture is filled in the second member 408 and the expandable member 404 without escaping or leaking back into the first member 406.

Figure 13A:
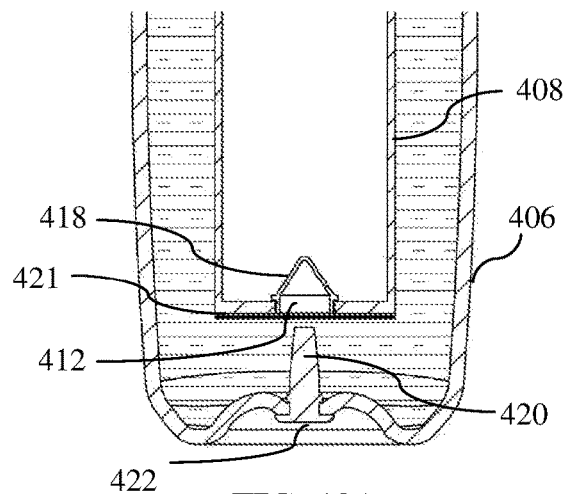
FIGS. 13A to 13F depict schematic drawing of a lower or bottom portion of the device shown in FIG. 4 with various components/members thereof at various states.
Figure 13B:
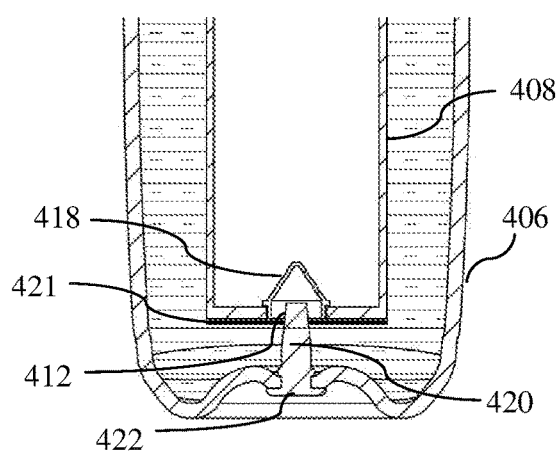
Figure 13C:
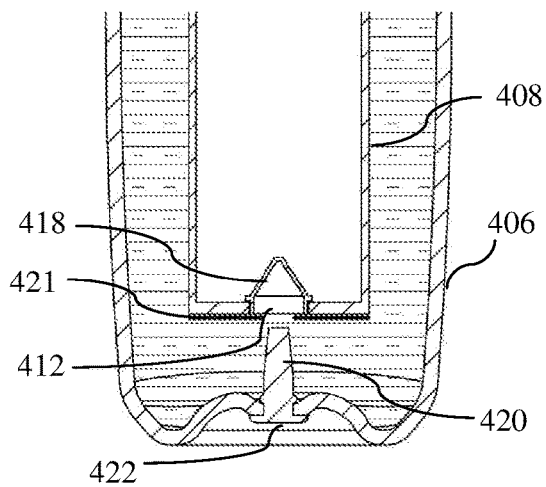
Figure 13D:
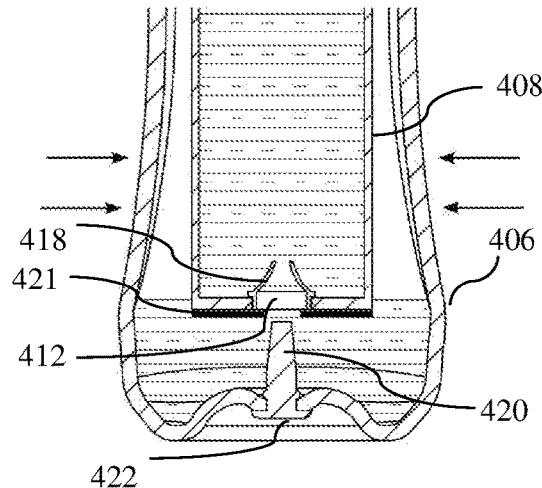
Figure 13E:
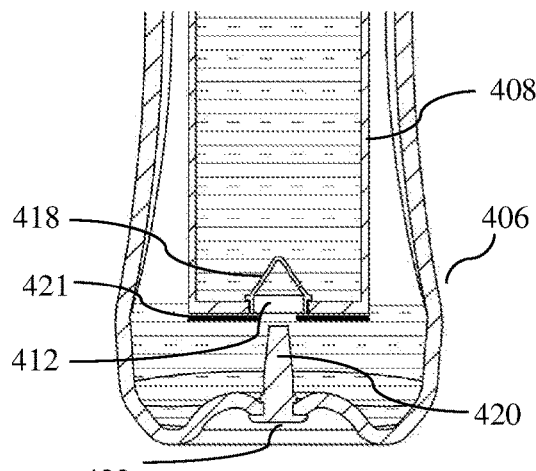
Figure 13F:
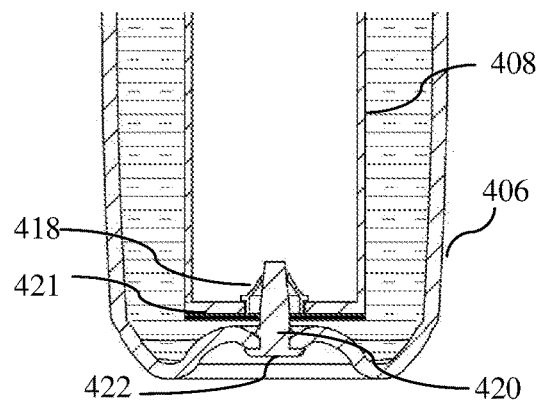

FIGS. 13A to 13F depict schematic drawing of a lower or bottom portion of the device 400 in greater detail to better illustrate various components/members thereof at various states. In various embodiments, the valve 418 may be adjustable or modifiable to be in one of a plurality of states as illustrated in FIG. 13A to 13F. As mentioned above, in a first state (e.g., when the first member 406 is compressed to perform treatment as shown in FIG. 13D), the valve 418 functions to provide one-directional fluid flow through the valve 418 from the first member 406 to the second member 408. In a second state (e.g., when deflating the expandable member 404 to remove the insertion member 402 from the body cavity as shown in FIG. 13F), the valve 418 may be deformed by an applied force (e.g., deliberate deformation of the valve 418 via user action or other mechanism) to allow fluid flow through the valve 418 from the second member 408 to the first member 406 for deflating the expanded expandable member 404. Various exemplary techniques for deforming the valve will be described later below according to various embodiments of the present invention.

In other embodiments, the valve may be made of a dissolvable (phase change) material configured to dissolve over a period of time after contact with fluid (e.g., the at least one of the first endothermic reactant and the endothermic product) and/or exposure to above a certain temperature (e.g., greater than about 30° C.) to be at the second state to allow fluid flow through the valve from the second member 408 to the first member 406 for deflating the expanded expandable member 404.

In various embodiments, the valve 418 may further be adjustable between the first state and a third state (e.g., prior to compressing the first member 406 as shown in FIG. 13A or after sufficient fluid has been delivered to the expandable member 404 as shown in FIG. 13C). In the third state, the valve 418 may remain closed and function as a barrier to prevent any fluid flow between the first member 406 and the second member 408. For example, the valve 418 may initially be at the third state and when activated via pressure or other mechanism, the valve 418 may switch to the first state and provide one-directional fluid flow through the valve 418 from the first member 406 to the second member 408. Once adequate substance has been delivered to the expandable member 404 to inflate it, the valve may switch back to the closed state as illustrated in FIG. 13E. This serves as an additional safety mechanism to prevent over expansion of the expandable member 404. The valve 418 may then also be adjusted to the second state as shown in FIG. 13F such as the valve 418 provides a one-directional fluid flow in the opposite direction from the second member 408 to the first member 406 to deflate the expandable member 404 and enable the insertion member 402 to be removed from the anal canal with ease and/or without causing discomfort to the patient.

In various embodiments, such as in the example embodiment of FIG. 5, a valve operable in the same or similar manner as described above may be provided within the insertion member (such as at an end portion thereof in the first member) for controlling fluid flow between the first member and the expandable member. For example, referred to FIG. 5C, as the valve 509 is operable as a one-way valve when the first and second members are compressed to perform treatment, fluid in the channel 510 and the expandable member 504 (e.g., the endothermic product that has flowed in) is prevented from flowing back into the first member 506, thereby maintaining the fluid in the expandable member 504 for maintaining the expandable member 504 in the expanded/inflated state. This also advantageously enables the cold therapy from the endothermic reaction to last longer as the endothermic reaction mixture is filled in the expandable member 504 without escaping or leaking back into the first member 506.

Separating Member (Separation Membrane)

In various embodiments, instead of or in addition to the valve described hereinbefore, the device comprises a separating (breakable) member configured to, in a first state (e.g., before the expandable member is inflated), block the first and second endothermic reactants from cooperating and, in a second state (e.g., when compressing the first member to inflate the expandable member), allow the first and second endothermic reactants to cooperate to effect an endothermic reaction.

In an example embodiment, the first member and the second member may be configured such that the first and second endothermic reactants contained respectively therein are separated by a separating membrane, such as, by a breakable membrane. In this regard, the separating membrane may configured to be breakable or capable of being fractured when the first member and/or the second member is compressed to a sufficient extent or with sufficient pressure so as to allow the first and second endothermic reactants to mix to effect the endothermic reaction. For example, as described hereinbefore with reference to FIGS. 5D to 5G, the second member 508 may comprise an opening 518 sealed by a separating member/membrane 520 as illustrated in FIGS. 5D and 5E, or the second member 508 may constitute a separating member/membrane as illustrated in FIGS. 5F and 5G (i.e., the second member itself is the separating member/membrane). In this regarding, the separating member/membrane is configured to, in a first state (e.g., an initial/original state before the expandable member 504 is inflated), block the first and second endothermic reactants from cooperating and, in a second state (e.g., in a compressed state after compressing the first and second members such that the separating member is broken), allow the first and second endothermic reactants to cooperate to effect the endothermic reaction.

In various embodiments, as for example illustrated in FIGS. 13A to 13F, the separating membrane 421 is arranged to seal an opening 412 of the second member 408 providing fluid communication between the first and second members. As shown in FIGS. 13A to 13F, in the example whereby the opening 412 is located at a bottom end of the second member 408, the separating member 421 may also be arranged on or applied to the bottom end of the second member 408. With this configuration, the separating member 421 is located between the valve 418 and the first member 408 (in particular, opposing the elongated or engaging member 420 (to be described below) of the first member 408). In operation, as illustrated in FIGS. 13A and 13C, the separating membrane 421 may be broken or pierced through by the elongated member 420 for unblocking the fluid communication path between the first and second members initially blocked by the separating membrane 421. The device 400 may then be initiated or activated (for endothermic reaction and inflation of the expandable member 404) by compressing the first member 406 as shown in FIG. 13D. For example, by arranging the separating membrane 421 between the valve 418 and the first member 406, the separating membrane 421 would be ruptured with a lower travel distance from the elongated or engaging member 420 for initiating the endothermic reaction (activating the device).

Activation Mechanism

In various embodiments, the device comprises an activation mechanism for enabling the first and second endothermic reactants to cooperate to effect the endothermic reaction, such as, by breaking or fracturing the separating member 421 blocking the first and second endothermic reactants from cooperating. For example, referring to the device 400 shown in FIGS. 4A to 4B and 13A to 13F, the activation mechanism may comprise an elongated or engaging member 420 connected to or extending from a depressable portion 422 of the first member 406 such that the elongated member 420 fractures or pierces through the separating member 421 when the depressable portion 422 is depressed, e.g., by a user. As shown in FIGS. 13A to 13F, the elongated structure 420 may extend along a longitudinal axis of the device 400 and towards the separating member 421. The depressable portion 422 may be an elastic shape-memory member or a compressible spring-like member such that upon an applied pressure thereon, the depressable portion 422 is depressed and upon removal of the applied pressure thereon, the depressable portion 422 reverts back to its original/initial shape or form For example, as illustrated in FIGS. 13A to 13F, the depressable portion 422 may be an indented for form an indented portion, which advantageously protects the activation mechanism from any accidental activation.

De-Activation Member

In various embodiments, the device comprises a de-activation (or de-expanding/contracting) mechanism for enabling the insertion member to be withdrawn from the body cavity after treatment is completed with ease and/or without discomfort to the patient. In particular, the deactivation mechanism is initiated to allow fluid flow from the expandable member and/or the second member to the first member so as to deflate the expandable member, and thus enabling easy withdrawal of the insertion member from the anal canal after the treatment is completed.

In an example embodiment, the de-activation member may comprise an absorbent member, such as a sponge-like member. For example, in the example embodiment of FIG. 4, the absorbent structure may be contained within the insertion member 402 or in the second member (internal component) 408 near or adjacent the channel 410 of the insertion member 402. The absorbent member may gradually absorb the substance (fluid) that is introduced into the expandable member. As another example, in the example embodiment of FIG. 5, the absorbent structure may be contained within the first member 506, preferably near or adjacent the channel 510 of the insertion member 502. If the absorbent member is located in the first member, the absorbent member can function to create a negative pressure within fluid communication path between the expandable member and itself. This can thus allow the substance (fluid) to gradually travel toward the absorbent member located in the first member or via capillary action. The absorption of the fluid/liquid from the expandable member would cause contraction and the reduction of the size of the expandable member, thus allowing easy removal of the insertion member from the body cavity.

In an example embodiment, the valve may also constitute a deactivation member. For example, as described hereinbefore, the valve may be deformed by an applied force to allow fluid flow through the valve from the expandable member and the second member to the first member to deflate the expanded expandable member. That is, the valve (e.g., pressure sensitive valve) may act as the deactivation member, whereby the deliberate deformation of the valve via user action or other mechanism would cause/allow the flow of the fluid (liquid) back into the first member at the end of the treatment. In various embodiments, structures may be placed adjacent to the valve that users would interact to cause the deformation of the valve.

For example, the deactivation member may be a rod or string-like member that is attached to the valve at one end and may be pulled by a user at the other end. Therefore, pulling the deactivation member would stretch/deform the valve and open the valve to allow fluid flow from the expandable member and the second member to the first member.

In an example embodiment, as described hereinbefore, the valve may be made of a dissolvable/degradable material configured to dissolve over a period of time after contact with fluid (e.g., the at least one of the first endothermic reactant and the endothermic product) and/or exposure to above a temperature threshold to allow fluid flow through the valve from the expandable member to the first member for deflating the expanded expandable member. For example, in the example embodiment of FIG. 4, a degraded valve would allow fluid to flow from the expandable member 404 and the second member 408 to flow to the first member 406. On the other hand, in the example embodiment of FIG. 5, a degraded valve would allow fluid to flow from the expandable member 504 to the first member 506. With this configuration, the deactivation can be automatically triggered after a period of time (e.g., at the end of the treatment) based on the time taken for the dissolvable/degradable material to dissolve/degrade after, e.g., contact with fluid.

In an example embodiment, the deactivation mechanism may also be realized by the activation mechanism described hereinbefore. That is, the activation and deactivation mechanisms comprise the same component(s)/member(s), and in particular, the elongated or engaging member. For example, the first time the depressable portion is depressed may constitute the activation mechanism and the second time the depressable portion is depressed may constitute the deactivation mechanism. That is, for example, the device may be activated by pressing the depressable portion 422 a first time as shown in FIG. 13B, and the device may subsequently be deactivated by pressing the depressable portion 422 again as shown in FIG. 13F.

Endothermic Reaction (Cold Therapy)

In various embodiments, in addition to applying pressure to tissues within the body cavity, a cold therapy is applied to the tissues as described hereinbefore to improve the effectiveness of the treatment. In various embodiments, the cold therapy is applied by the expandable member receiving the endothermic product generated by the endothermic reaction or dissolution of the first and second endothermic reactants. For example, in the case of the first and second endothermic reactants being stored separated in the device and being separated by a separating membrane, the endothermic reaction or dissolution may be initiated when the membrane separating the endothermic reactants is caused to break or punctured.

As described hereinbefore, according to various embodiments, one of the at least two endothermic reactants is contained the first member and another of the at least two endothermic reactants is contained in the second member, and whereby an endothermic reaction between the first and second endothermic reactants may occur in the first member and the endothermic product may then be delivered through a channel in the insertion member to the expandable member. As also mentioned hereinbefore, it will also be appreciated to a person skilled in the art that a first endothermic reactant and a second endothermic reactant cooperating to effect an endothermic reaction is not limited to involving only the first and second endothermic reactants, and can include additional endothermic reactant(s) as long as the endothermic reaction involves at least the first and second endothermic reactants.

In various embodiments, the device may comprise one or more channels configured to circulate the endothermic product (cold therapy fluid) in and out of the anorectal region. The reservoir member may comprise a first (start) reservoir and a second (end) reservoir, and the first and second reservoirs may be connected via a channel that extends within and circulate through the insertion member. For example, the start component may contain the endothermic reactants to effect the endothermic reaction and the end reservoir may comprise an absorbent member configured to draw or pull in the endothermic product (cold therapy fluid) via capillary action. The one or more channels may also comprise absorbent member(s) that would facilitate capillary action. For example and without limitation, the absorbent member may be made of nitrocellulose, porous paper or sintered polymer.

By way of examples only and without limitations, exemplary first and second endothermic reactants and the associated endothermic reactions are provided in Table 1 below.

TABLE 1

Exemplary first and second endothermic reactants and the associated endothermic reactions

| Common Name | Balanced Chemical Equation | Enthalpy |
| --- | --- | --- |
| Barium Hydroxide Octahydrate + Ammonium Thiocyanate | $Ba(OH)_2 \cdot 8H_2O_{(s)} + 2NH_4SCN_{(s)} \rightarrow Ba(SCN)_{2(s)} + 10H_2O_{(l)} + 2NH3_{(g)}$ | +80 kJ/mol |
| Barium Hydroxide Octahydrate + Ammonium Chloride | $Ba(OH)_2 \cdot 8H_2O_{(s)} + 2NH_4Cl_{(s)} \rightarrow Ba(Cl)_{2(s)} + 10H_2O_{(l)} + 2NH3_{(g)}$ | +63.6 kJ/mol |
| Barium Hydroxide Octahydrate + Ammonium Nitrate | $Ba(OH)_2 \cdot 8H_2O_{(s)} + 2NH_4NO_{3(s)} \rightarrow Ba(NO_3)_{2(s)} + 10H_2O_{(l)} + 2NH3_{(g)}$ | +61.6 kJ/mol |
| Urea + Water | $(CONH_2)_{2\ (s)} \rightarrow (CONH_2)_{2\ (aq)}$ | +15.1 kJ/mol |
| Ethanoic Acid + Sodium Carbonate | $2CH_3COOH_{(aq)} + Na_2CO_{3(s)} \rightarrow H_2O_{(l)} + CO_{2(g)} + 2Na^+CH_3COO^-_{(aq)}$ | +0.861 kJ/mol |
| Ammonium Chloride + Water | $NH_4Cl_{(s)} \rightarrow NH_4^+{}_{(aq)} + Cl^-{}_{(aq)}$ | Solution: +14.78 kJ/mol |
| Ammonium Nitrate + Water | $NH_4NO_{3\ (s)} \rightarrow NH4^+{}_{(aq)} + NO_3^-{}_{(aq)}$ | Solution: +19.25 kJ/mol |
| Potassium Chloride + Water | $KCl_{(s)} \rightarrow K^+{}_{(aq)} + Cl^-{}_{(aq)}$ | Solution: +17.22 kJ/mol |

User Activation Mechanism

In various embodiments, the device may be initiated/activated by a user or operator to initiate the endothermic reaction of the endothermic reactants and the inflation of the expandable member once the insertion member has been inserted into the correct/desired position/location in the anal canal/rectum over the hemorrhoids. In various embodiments, the user activation mechanism may comprise a squeezable/compressible bottle or container bag such that a simple one-step squeeze action by the user will deliver the substance (e.g., liquid or air/gas) contained in the first/reservoir member into or initiate the mechanical movement of the expandable member. This will result in the expansion of the expandable member as described hereinbefore. In various embodiments, the squeezing action may generate enough pressure to cause a change in the state of the valve member and/or the separation membrane to allow inflow of the substance (e.g., liquid or air/gas) from the first member into the expandable member. In another embodiment, the user activation mechanism may comprise a biodegradable outer sheath such that the biodegradable outer sheath would be dissolved by the liquid within the anorectal region and automatically activate and deploy the expandable member that is initially contained or secured within the outer sheath. In yet another embodiment, the user activation mechanism may comprise a solid outer sheath such that mechanically adjusting or pulling the outer sheath would activate and deploy the expandable member initially contained or secured within the outer sheath, for example, as shown in FIG. 12.

Housing/Frame Structure

Figure 14:
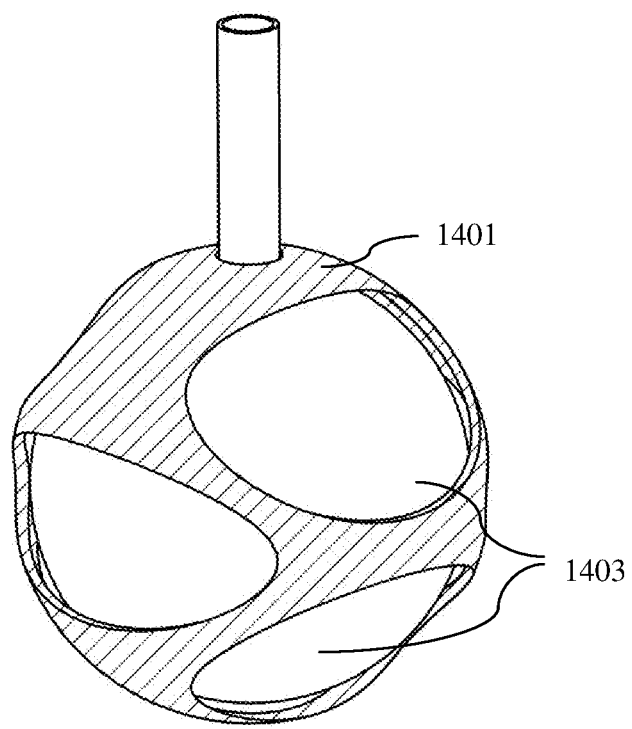
FIG. 14 depicts a schematic drawing of a structure for housing/holding the first member according to an example embodiment of the present invention.

In various embodiments, the device further comprises a structure for housing/holding the first member (reservoir member). For example, in various embodiments, the first member may be in the form of a flexible container bag, such as a foil bag, for storing/holding the first endothermic reactant therein, and the housing/frame structure may constitute an external loader designed/configured to compactly contain the first member. In this regard, prior to inserting the insertion member into the body cavity, the user may place the first member into the external loader. For example, the structure may be made of a firm material (e.g., plastic) for enabling the user to hold the device without premature/accidental activation (e.g., accidental compression) of the expanding member by the user (e.g., when inserting the insertion member into the body cavity). Once the insertion member has been inserted into the correct position over the hemorrhoids, in various embodiments, the user may compress the first member being held within the external loader to activate the device and inflate the expandable member. In various other embodiments, the structure 1401 may have window(s)/opening(s) 1403 as shown in FIG. 14 for allowing the user to access and physically compress the first member therein using, e.g., their fingers or appropriate tools.

FIG. 15A depicts a schematic perspective view of the device having a structure 1500 for housing the first member 1506 according to an example embodiment of the present invention. It will be appreciated that the structure 1500 is not limited to the configuration as shown in FIG. 15A, and can be modified as appropriate or desired. For example, FIG. 15B depicts a schematic perspective view of the device having another structure 1501 for housing the first member 1506 according to another example embodiment of the present invention. FIGS. 15C to 15E depict a schematic side view of the device of FIG. 15B at various states. The structure 1500/1501 comprises a latch mechanism 1503 configured to be releasably lockable between a lock state and a release/relax state. In particular, in the lock state, the structure 1500/1501 is configured to apply compressing pressure to compress the first member 1506 and maintain/hold the first member 1506 in a compressed state, and in the release state, the structure 1501 is configured to house the first member 1506 without applying compressing pressure thereto. For example, as shown in FIGS. 15A to 15E, the structure 1500/1501 may comprise two flap or clam portions 1505 fixed together at one end 1507 and releasably lockable at another end (e.g., opposing the one end) such that the two flap portions 1505 may be compressed/squeezed by the user to compress the first member 1506 housed therein and locked in position by the latch mechanism 1503 to inflate the expandable member 1504 as shown in FIG. 15D. The structure 1500/1501 is also preferably made of a pre-formed or shape-memory material such that upon releasing the latch mechanism 1503, the structure 1500/1501 would revert to its original/initial shape/form (the release state) to relief/release the first member 1506 from being compressed as shown in FIG. 15E. As also shown in FIG. 15E, releasing the first member 1506 from being compressed may also activate the deflation of the expandable member 1504.

In various embodiments, as for example illustrated in the structure 1501, one of the two flap portions 1505 (first flap portion) comprise an engaging arm 1510 configured for engaging with the other of the two flap portions 1505 (second flap portion) to adjustably maintain the structure in the lock state and release state. In particular, the engaging arm 1510 comprises a first engaging portion 1512, such as a slot or a groove, for receiving an end of the second flap portion to releasably hold the structure in the lock state, and a second engaging portion 1514, such as a bump or a protrusion, for engaging with the end of the second flap portion to provide some degree of resistance or restriction for the second flap portion to move to compress the first member 1506. Therefore, the second engaging portion 1514 is able to maintain the structure 1501 in the release/relax state until a sufficient amount of pressure/force is applied to overcome the resistance provided by the second engaging portion 1514, and is thus advantageously able to prevent or minimize accidental compression, for example, when holding the device 1500. It will be appreciated to a person skilled in the art that the first and second engaging portions are not limited to the configurations as illustrated in FIGS. 15A and 15B, and other locking/engaging mechanisms achieving the same or similar function are also within the scope of the present invention.

Figure 16:
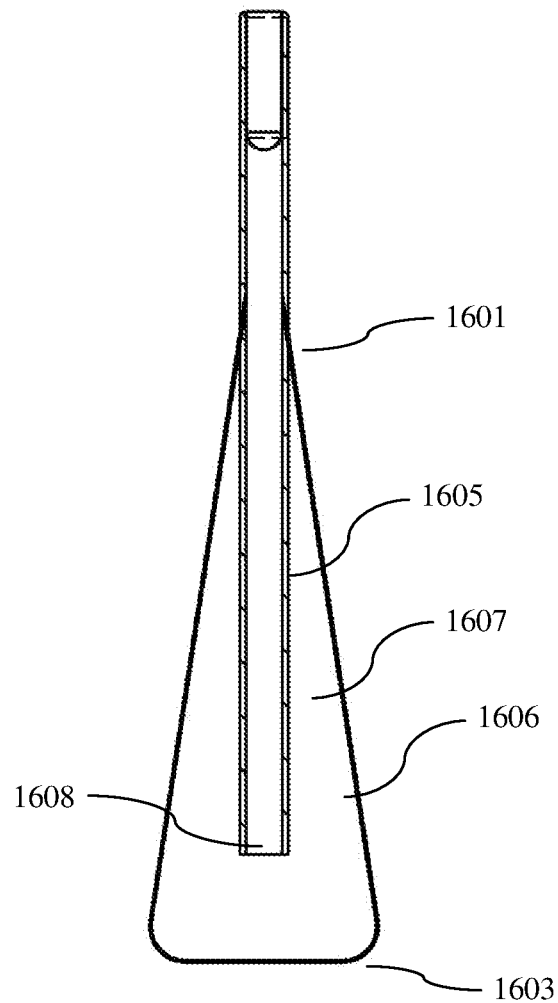
FIG. 16 depicts a schematic drawing of a device for insertion into a body cavity whereby an internal column extends into the first member according to various embodiments of the present invention.

In various embodiments, the internal compartment or internal column is configured such that it extends at least about 10% of a height/length of the first member 1606 (e.g., between a top end/region 1601 and a bottom end/region 1603 of the first member) into the first member 1606 from the top end/region 1601. For example, FIG. 16 is a schematic drawing of the device illustrating the internal compartment/internal column 1605 extending about ⅘ of the height of the first member 1606 into the first member 1606 from the top end/region 1601 according to an example embodiment. Such a configuration reduces/minimises air from entering into the expandable member, which is advantageous since unwanted air entry may impede the delivery of the endothermic product (cold therapy) into the expandable member. In particular, with such a configuration, a space/region 1607 is provided in the first member at a level above a bottom end opening 1608 of the internal column 1605. Therefore, air introduced (e.g., undesirable seeping of air into the first member 1606) would be trapped/held in such a space due to the lighter weight of air. This improves the ability of the fluid (liquid) in the first member 1606 to enter the internal column 1605 and then into the expandable member, thereby delivering better cold therapy.

In various embodiments, the device may further comprise a secondary valve (pressure sensitive valve) that opens when pressure within the expandable member is above a predetermined/predefined threshold, such as above about 300 to 400 mmHg. As an example, the second member (e.g., internal/reaction chamber 408) may comprise the secondary valve at an appropriate location/portion that opens to enable release of fluid out of the second member thereby releasing the pressure. For example and without limitation, the secondary valve may have an umbrella shape that has flexible flaps, or be a plug-like member that is configured to move away from the second member (or open) to release the pressure if the pressure exceeds a predetermined threshold.

In various embodiments, the device may further comprise a re-use prevention mechanism as a safety feature to prevent the reuse of the device which may harm users due to, for example, hygiene reasons. In various embodiments, the second member comprises clogging agents for clogging fluid communication to the expandable member upon exposure to the first endothermic product over a period of time so as to prevent the reuse of the device. The clogging agents are configured to prevent the inflow of substance (fluid) into the expandable member after the device has already been used (i.e., the expandable member has already been inflated at least once before). For example, the clogging agent may be made of highly absorbent material such sodium polyacrylate. The material would function to absorb the liquid and expand to clog the fluid communication path to the expandable component. In an embodiment, the sodium polyacrylate also acts as a secondary safety mechanism which would gradually absorb liquid from the expandable component. This would prevent the extended use of the product which may cause harm. It would also enable the expandable component to deflate if the deflation mechanism fails.

In various embodiments, the device is configured such that the insertion member is disposable (e.g., for one time use) and the body of the device (e.g., including the first and second members) can be separated from the insertion member. For example, the first member may be a squeezable/compressible bottle that the user is able to re-fill with a fluid (e.g., first endothermic reactant) that creates the endothermic reaction. In various other embodiments, the insertion member and the first and second members may be disposable, and can be separated from the housing/frame structure of the device.

In various embodiments, the insertion member may have a fluid communication with the first and second members of the device via a conduit (e.g., flexible conduit). For example, this configuration enables the patient to sit (or be in other positions) after the insertion member has been inserted, thus providing a more comfortable treatment for the patient.

Figure 17A:
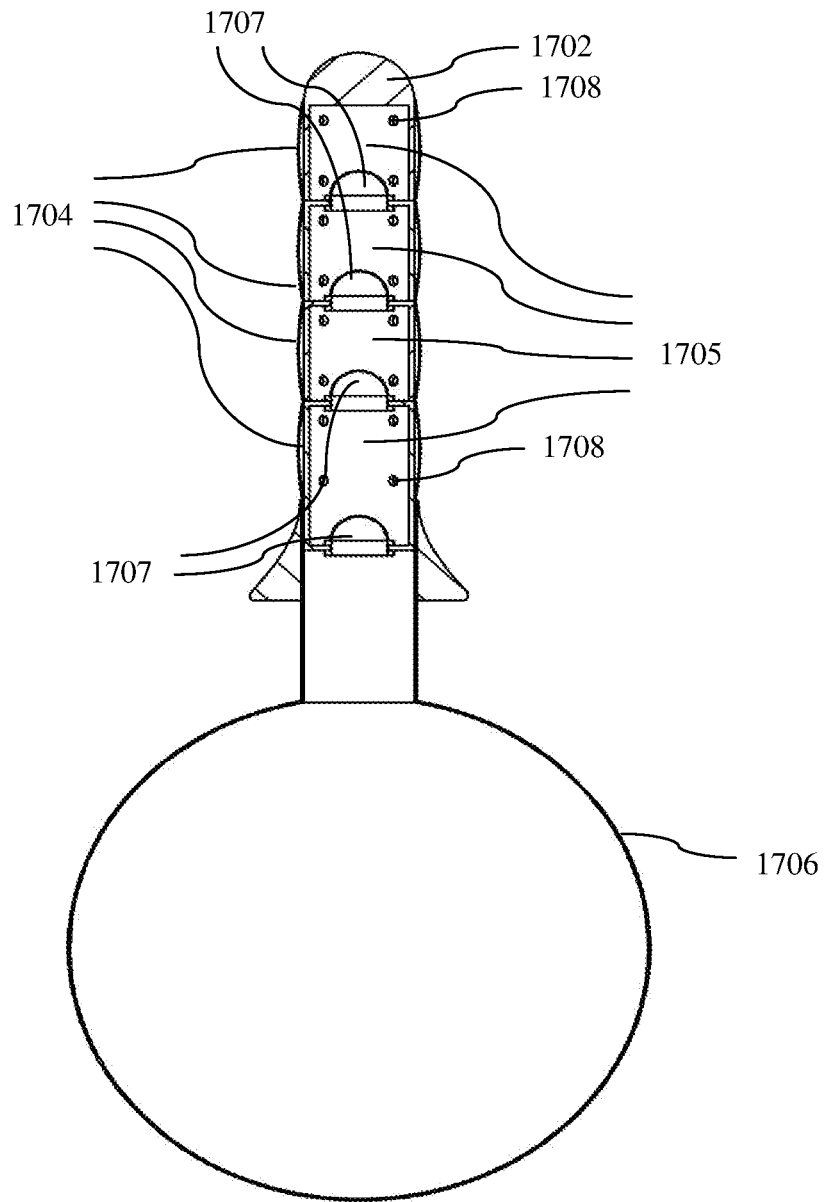

FIGS. 17A to 17C depict a schematic drawing of a device according to various embodiments of the present invention. In particular, the insertion member 1702 of the device is configured to comprise a plurality of compartments 1705 arranged successively along the insertion member 1702, each compartment 1705 having coupled therewith a respective expandable member 1704. Each expandable member 1704 is also capable of being expanded in response to the at least one of the first or second endothermic reactant and the endothermic product received from the respective compartment 1705. A plurality of valve 1707 is arranged in the channel of the insertion member 1702, and each valve 1707 is arranged between adjacent compartments 1705 associated therewith and configured to allow the at least one of the first or second endothermic reactant and the endothermic product to flow through the valve from a first compartment of the adjacent compartment to a second compartment of the adjacent compartments when a pressure acting on the valve 1707 is equal to or exceeds a threshold pressure, whereby the first compartment is closer to the first member 1706 than the second compartment.

For example, such a configuration of the expandable member 1704 advantageously addresses a problem whereby people may have different lengths of anal canal (e.g., ranging from about 1 cm to about 5 cm in length). Therefore, the device (in particular, the insertion member) can advantageously accommodate various anal canal lengths in a safe manner and yet be effective in tamponading and delivering cold therapy to the correct hemorrhoidal regions. As shown in FIG. 17A, the insertion member 1702 may comprise various pressure activated valves 1707 situated along the longitudinal axis of the device such that the valves 1707 open at an appropriate location considering the individual sphincter length. Through-holes (vents) 1708 of various shapes such as elliptical shapes can be created in the vicinity of the valves. The through-holes allow fluids to fill up the balloon. Upon activation of the device and fluid is squeezed up the catheter-like device (insertion member) 1702, if the sphincter is in contact with the through-holes, the fluid will minimally escape from the catheter core. Instead, the fluid will flow further upwards and escape from a vent further up the sphincter area. This mechanism ensures that the balloon will only be deployed at the region near the sphincter next to the hemorrhoids, thereby accommodating different anal canal sizes.

FIG. 17B depicts the state of the insertion member 1702 in an example where the patient's anal canal is relatively short, such as about 2 cm. In this example, the compression of the first member 1706 by the user would increase the pressure in the reservoir and cause the first valve 1710 to open. This causes the first balloon compartment to open and apply pressure on the hemorrhoids. The remaining valves 1712, 1714, 1716 would remain closed as the pressure in the first compartment remains below the pressure required to open any of the remaining valves.

FIG. 17C depicts the state of the insertion member 1702 in an example where the patient's anal canal is longer, such as about 4 cm. In this example, the compression of the first member 1706 by the user would increase the pressure in the reservoir and cause the first valve 1710 to open. The longer anal canal applies external pressure on the first compartment balloon/bladder. This disrupts the balloon from expanding fully which leads to build up pressure in the first compartment. The increased pressure on the next (second) valve 1712 causes the second valve 1712 to open and subsequently the expansion of the second compartment bladder/balloon. The remaining valves 1714, 1716 remain closed as the pressure in the second compartment remains below the pressure required to open any of the remaining valves.

Accordingly, various embodiments of the present invention provide a simple one-step squeeze maneuver that will activate a synergistic, dual action of an expanding mechanism and instant cold therapy to safely tamponade and induce vasoconstriction of hemorrhoidal blood vessels to immediately arrest bleeding from hemorrhoids. Various embodiments also provide a device to instantaneously cool and compress the anal canal tissue using a small insertion dimension and a method of targeted compression on the hemorrhoid tissue with minimal expansion volume.

Figure 18:
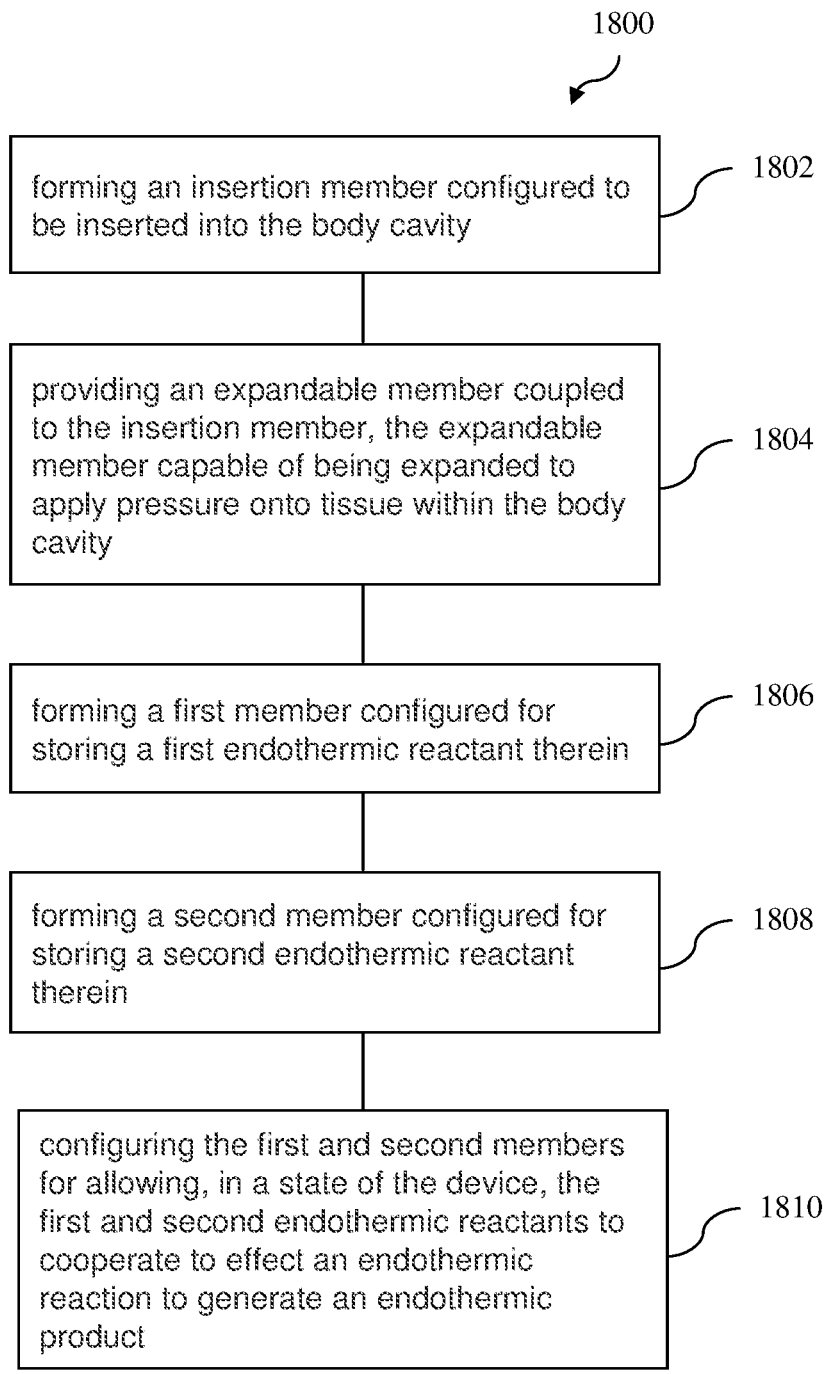
FIG. 18 depicts a schematic diagram illustrating a method of fabricating a device for inserting into a body cavity according to various embodiments of the present invention.

FIG. 18 depicts a schematic diagram illustrating a method 1800 of fabricating a device for inserting into a body cavity according to various embodiments of the present invention. The method includes a step 1802 of forming an insertion member configured to be inserted into the body cavity, a step 1804 of providing an expandable member coupled to the insertion member, the expandable member capable of being expanded to apply pressure onto tissue within the body cavity, a step 1806 of forming a first member configured for storing a first endothermic reactant therein, a step 1808 of forming a second member configured for storing a second endothermic reactant therein, and a step 1810 of arranging the first and second members for allowing the first and second endothermic reactants to cooperate to effect an endothermic reaction to generate an endothermic product. Furthermore, the step 1804 of providing the expandable member further comprises configuring the expandable member to receive at least one of the first or second endothermic reactant and the endothermic product through a channel within the insertion member. It will be appreciated that the steps described above may be performed in any order as appropriate/desired and are not limited to the order presented.

Various embodiments of the present invention have been described hereinbefore whereby the cold therapy applied by the expandable member as a result of an endothermic reaction before two endothermic reactants. While this is preferred in such embodiments, in other embodiments of the present invention, the cold therapy may be achieved by other means. In an example embodiment, the cold may be generated by a phase change material, such as but not limited to, hydrated sodium sulphate (mirabilite) (phase change at about 18° C.) and paraffin 18-carbons (phase change at about 28° C.). For example, the phase change material may have a melting temperature close to anorectal temperature. When inserted into the anorectal region, the phase change material would melt and absorb the heat from the surrounding, hence cooling the hemorrhoids. In another example embodiment, the device may comprise a compressible reservoir member including a fluid (liquid) and the reservoir member may be placed in a refrigerator to reduce the temperature of or chill the fluid contained therein. After the fluid has been cooled to a desired temperature, the device may then ready for use in treatment. In particular, cold therapy may be applied to the hemorrhoidal regions in the anal canal by the expandable member receiving the chilled fluid after the reservoir has been compressed to initiate treatment.

Figure 19:
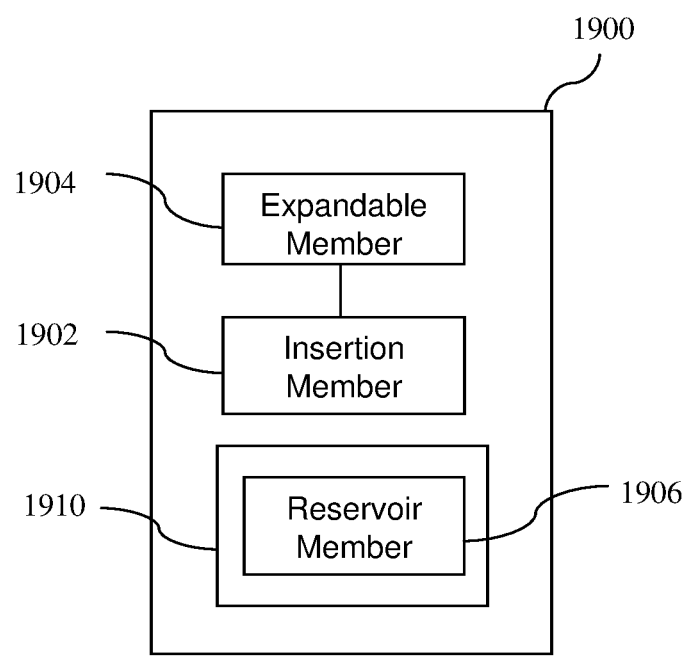
FIG. 19 depicts a schematic drawing of a device for insertion into a body cavity according to various embodiments of the present invention.

Therefore, according to various embodiments of the present invention, there is provided a device 1900 as shown in FIG. 19 comprising an insertion member 1902 configured to be inserted into the body cavity, an expandable member 1904 coupled to the insertion member 1902 whereby the expandable member 1904 is capable of being expanded to apply pressure onto tissue within the body cavity, a reservoir member 1906 configured for storing a fluid (liquid) therein. In particular, the expandable member 1904 is configured to receive the fluid through a channel within the insertion member 1902. Preferably, in such embodiments, the device 1900 comprises a structure 1910 for housing the reservoir member 1906 as described hereinbefore with reference to FIGS. 15A to 15E. In particular, the structure 1910 comprises a latch mechanism configured to be releasably lockable between a lock state and a release state. In the lock state, the structure 1910 is configured to apply compressing pressure to compress the reservoir member 1906 and maintain/hold the reservoir member 1906 in a compressed state, and in the release state, the structure 1910 is configured to house the first member without applying compressing pressure thereto.

As described hereinbefore, the expandable member is configured to receive at least one of the first or second endothermic reactant and the endothermic product. FIGS. 20A to 20D depicts various configurations of the expandable member according to various example embodiments of the present invention.

Figure 20A:
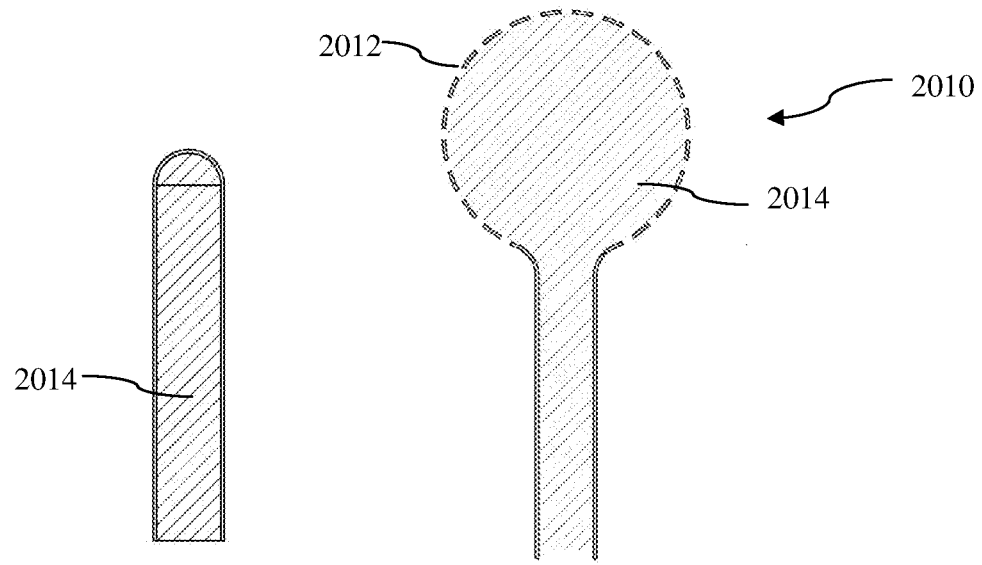
FIGS. 20A to 20D depict various configurations of the expandable member according to various example embodiments of the present invention.

FIG. 20A depicts a schematic drawing of an expandable member 2010 according to an example embodiment of the present invention. In the example embodiment, at least a portion of the expandable member 2010 comprises pores 2012 configured for allowing fluid (e.g., therapeutic substance or a mixture of the endothermic product and the therapeutic substance) 2014 in the expandable member 2010 to discharge (seep out) through the pores 2012 for delivery of the therapeutic substance 2014 to the tissue within the body cavity. In this regard, the pores 2012 may expand or open (thus triggering the release of the fluid 2014) as the expandable member 2010 is inflated. For example, the fluid (in particular, liquid) may then irrigate the anal region for various purposes, such as to enable better bowel movement. The liquid may also be therapeutic in nature for various types of treatment as desired/appropriate. For example and without limitations, therapeutic substance may be in the form of agents, gels, hydrogels, drugs, and formulations.

Figure 20B:
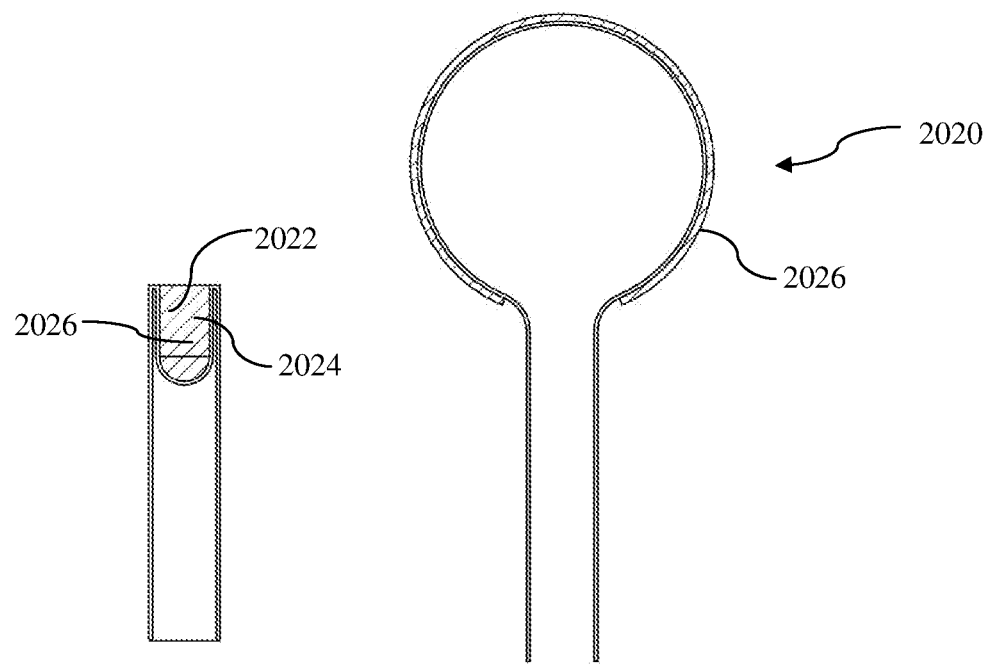

FIG. 20B depicts a schematic drawing of an expandable member 2020 according to an example embodiment of the present invention. In the example embodiment, the expandable member 2020 is configured such that, prior to being expanded, an outer surface 2022 of the expandable member 2020 defines a receptacle 2024, the receptacle 2024 configured for storing a therapeutic substance 2026 therein for delivery to the tissue within the body cavity when the expandable member 2020 is expanded. For example, the expandable member 2020 may be stored in a folded or collapsed state within a channel of the insertion member, and the expandable member 2020 in the folded state defines or serves as a reservoir for holding a therapeutic substance 2026. For example, the therapeutic substance 2026 may be in a liquid form initially held within the receptacle 2024, or may be in the form of a layer (e.g., film or mesh) applied to or disposed on the outer surface 2022 of the expandable member 2026. In various embodiments, a removable lid or cap (not shown) may also be placed at a top end of the insertion member to cover the receptacle 2024.

Figure 20C:
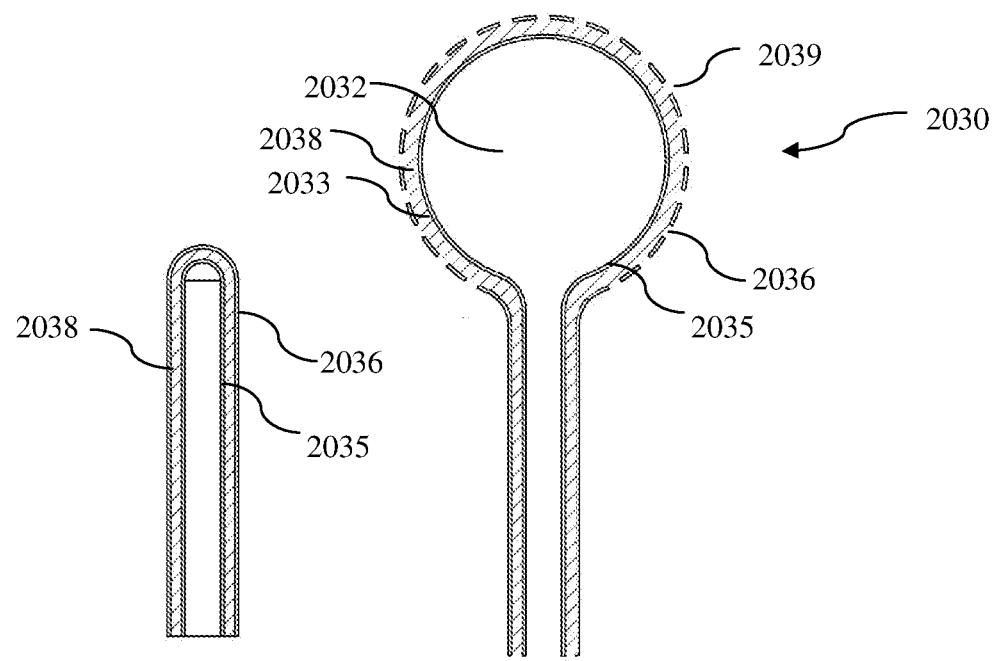
Figure 20D:
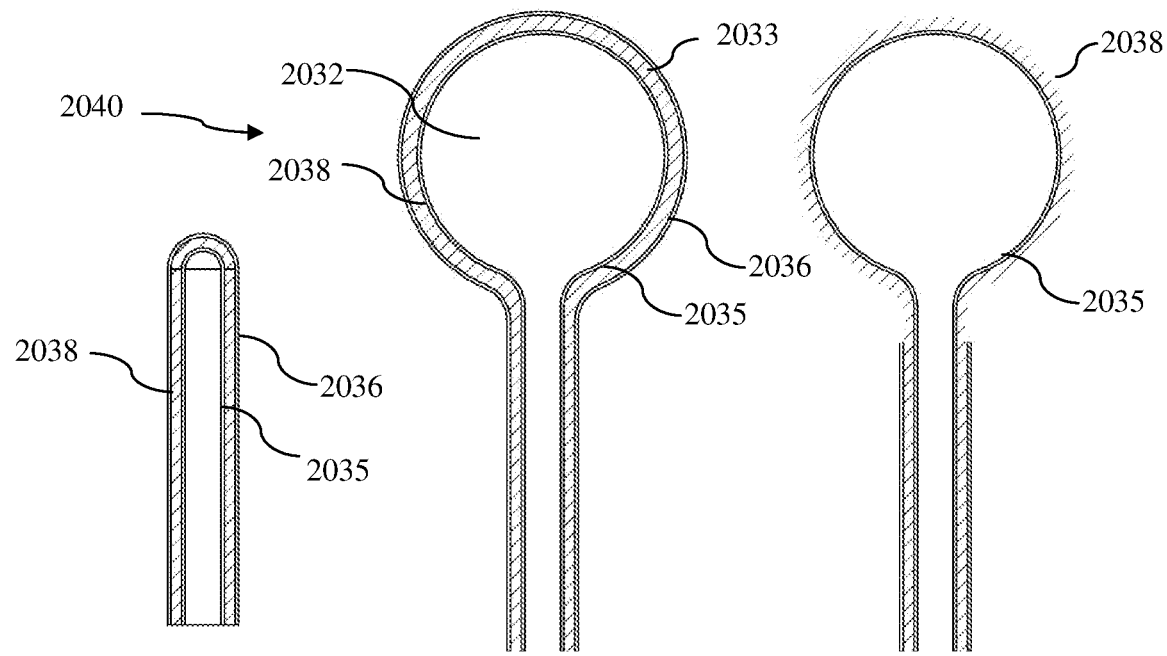

In various embodiments, the expandable member may comprise a plurality of compartments. For example, one of the compartments may be configured to receive the first or second endothermic reactant and/or the endothermic product to, for example, expand the expandable member and/or to deliver a cold therapy, while another one or more of the compartments may be configured to receive or have stored therein fluid (in particular, liquid) for delivering irrigation and/or therapeutic substance to the anal region through the pores of such compartment(s). FIG. 20C depicts a schematic drawing of an expandable member 2030 according to an example embodiment of the present invention comprising a first or inner compartment 2032 and a second or outer compartment 2033. In particular, the expandable member 2030 comprises a first or inner expandable layer 2035 and a second or outer expandable layer 2036. As shown, the inner expandable layer 2035 is arranged or disposed within the outer expandable layer 2036, and the inner expandable layer 2035 and the outer expandable layer 2036 are configured to provide an outer compartment 2033 for storing a therapeutic substance 2038 therebetween for delivery of the therapeutic substance to the tissue within the body cavity. In the example embodiment of FIG. 20C, the second or outer expandable layer 2036 comprises pores 2039 configured for allowing the therapeutic substance 2038 between the inner expendable layer 2035 and the outer expandable layer 2036 to discharge (seep out) through the pores 2039 for delivery of the therapeutic substance to the tissue within the body cavity. In particular, the therapeutic substance 2038 contained within the outer compartment 2033 may be delivered through the pores 2039 which expand or open (thus triggering the release of the therapeutic substance 2038) as a result of the pressure exerted by the inner compartment 2032 on the therapeutic substance 2038 as the inner compartment 2032 is inflated. In another example embodiment as shown in FIG. 20D, at least a portion of the outer expandable layer 2036 is made of a biodegradable material for allowing the therapeutic substance 2038 between the inner expendable layer 2035 and the outer expandable layer 2036 to escape for delivery of the therapeutic substance 2038 to the tissue within the body cavity when the biodegradable material is degraded.

Throughout the present specification, it should also be understood that any terms such as "top", "bottom", "base", "down", "sideways", "downwards", or the like, when used in the present specification are used for convenience and to aid understanding of relative positions or directions, and not intended to limit the orientation of the devices described herein.

While embodiments of the invention have been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:

1. A device for insertion into a body cavity, the device comprising:
   an insertion member configured to be inserted into the body cavity;
   at least one expandable member coupled to the insertion member, the at least one expandable member capable of being expanded to apply pressure onto tissue within the body cavity;
   a first member configured for storing a first endothermic reactant therein; and
   a second member configured for storing a second endothermic reactant therein,
   wherein the first and second members are configured to, in a state of the device, allow the first and second endothermic reactants to cooperate to effect an endothermic reaction to generate an endothermic product,
   wherein the at least one expandable member is configured to receive at least one of the first endothermic reactant, the second endothermic reactant and the endothermic product through a channel within the insertion member,
   wherein at least the first member is configured to be compressible to cause the device to be in said state, wherein compressing the first member reduces a volume within the first member, thereby forcing the first endothermic reactant stored in the first member and/or the second endothermic reactant stored in the second member to flow to cooperate with each other to effect the endothermic reaction, and pressuring the at least one of the first endothermic reactant, the second endothermic reactant and the endothermic product to flow through the channel into the at least one expandable member for expanding the at least one expandable member, and
   wherein the insertion member comprises a plurality of compartments arranged successively along the insertion member, each compartment having coupled therewith a respective expandable member, each of the respective expandable members capable of being expanded in response to the at least one of the first endothermic reactant, the second endothermic reactant and the endothermic product received from the respective compartment, wherein a plurality of valves are arranged in the channel of the insertion member, each valve arranged between adjacent compartments associated therewith and configured to allow the at least one of the first endothermic reactant, the second endothermic reactant and the endothermic product to flow through the valve from a first compartment of the adjacent compartments to a second compartment of the adjacent compartment when a pressure acting on the valve is equal to or exceeds a threshold pressure, the first compartment being closer to the first member than the second compartment.

2. The device according to claim 1, wherein the first member has stored therein the first endothermic reactant, and the second member has stored therein the second endothermic reactant, separately from the first endothermic reactant.

3. The device according to claim 1, comprising a separating member configured to, in a first state, block the first and second endothermic reactants from cooperating and, in a second state, allow the first and second endothermic reactants to cooperate to effect the endothermic reaction.

4. The device according to claim 3, wherein the separating member is configured to be breakable to change from the first state to the second state.

5. The device according to claim 4, wherein an opening of the second member is sealed by the separating member or the second member constitutes the separating member.

6. The device according to claim 1, wherein the second member is located within the first member and is configured to be compressible to cause the device to be in said state, wherein compressing the first member at a region where the second member is located also compresses the second member, thereby reduces a volume within the second member and causes the separating member to break to allow the second endothermic reactant stored in the second member to flow out of the second member and into the first member to cooperate with the first endothermic reactant to effect the endothermic reaction.

7. The device according to claim 1, wherein the second member is located within the first member and is configured to be non-compressible, wherein compressing the first member reduces the volume within the first member, thereby forcing the first endothermic reactant stored in the first member to flow into the second member, via an opening in the second member, to cooperate with the second endothermic reactant stored in the second member to effect the endothermic reaction.

8. The device according to claim 1, further comprising a structure for housing the first member.

9. The device according to claim 8, wherein the structure comprises a latch mechanism configured to be releasably lockable between a lock state and a release state, and wherein in the lock state, the structure is configured to apply compressing pressure to compress the first member and maintain the first member in a compressed state, and in the release state, the structure is configured to house the first member without applying compressing pressure thereto.

10. The device according to claim 1, wherein at least a portion of the at least one expandable member comprises pores configured for allowing a therapeutic substance in the at last one expandable member to discharge through the pores for delivery of the therapeutic substance to the tissue within the body cavity.

11. The device according to claim 1, wherein the at least one expandable member comprises an inner expandable layer and an outer expandable layer, wherein the inner expandable layer is arranged within the outer expandable layer, and the inner expandable layer and the outer expandable layer are configured to provide an outer compartment for storing a therapeutic substance therebetween for delivery of the therapeutic substance to the tissue within the body cavity.

12. The device according to claim 11, wherein the outer expandable layer comprises pores configured for allowing the therapeutic substance between the inner expandable layer and the outer expandable layer to discharge through the pores for delivery of the therapeutic substance to the tissue within the body cavity.

13. The device according to claim 11, wherein at least a portion of the outer expandable layer is made of a biodegradable material for allowing the therapeutic substance between the inner expandable layer and the outer expandable layer to escape for delivery of the therapeutic substance to the tissue within the body cavity when the biodegradable material is degraded.

14. The device according to claim 1, wherein the at least one expandable member is configured such that, prior to being expanded, an outer surface of the at least one expandable member defines a receptacle, the receptacle configured for storing a therapeutic substance therein for delivery to the tissue within the body cavity when the at least one expandable member is expanded.

15. The device according to claim 1, further comprising a valve configured to, in a first state, provide one-directional fluid flow through the valve from the first member.

16. The device according to claim 1, further comprising an external expandable member coupled to the insertion member at a predetermined distance from the distal end region, the external expandable member capable of being expanded to apply pressure onto an external region of the body cavity.

17. The device according to claim 1, wherein the insertion member is configured so as to be adjustable in length.

18. A method of fabricating a device for inserting into a body cavity, the method comprising:
 forming an insertion member configured to be inserted into the body cavity;
 providing at least one expandable member coupled to the insertion member, the at least one expandable member capable of being expanded to apply pressure onto tissue within the body cavity;
 forming a first member configured for storing a first endothermic reactant therein; and
 forming a second member configured for storing a second endothermic reactant therein; and
 configuring the first and second members for allowing, in a state of the device, the first and second endothermic reactants to cooperate to effect an endothermic reaction to generate an endothermic product,
 wherein said providing the at least one expandable member comprises configuring the at least one expandable member to receive at least one of the first endothermic reactant, the second endothermic reactant and the endothermic product through a channel within the insertion member,
 wherein at least the first member is configured to be compressible to cause the device to be in said state, wherein compressing the first member reduces a volume within the first member, thereby forcing the first endothermic reactant stored in the first member and/or the second endothermic reactant stored in the second member to flow to cooperate with each other to effect the endothermic reaction, and pressuring the at least one of the first endothermic reactant, the second endothermic reactant and the endothermic product to flow through the channel into the at least one expandable member for expanding the at least one expandable member, and wherein said forming an insertion member comprises configuring the insertion member to comprise a plurality of compartments arranged successively along the insertion member, each compartment having coupled therewith a respective expandable member, each of the respective expandable members capable of being expanded in response to the at least one of the first endothermic reactant, the second endothermic reactant and the endothermic product received from the respective compartment, wherein a plurality of valves are arranged in the channel of the insertion member, each valve arranged between adjacent compartments associated therewith and configured to allow the at least one of the first endothermic reactant, the second endothermic reactant and the endothermic product to flow through the valve from a first compartment of the adjacent compartments to a second compartment of the adjacent compartment when a pressure acting on the valve is equal to or exceeds a threshold pressure, the first compartment being closer to the first member than the second compartment.

* * * * *